United States Patent
Gellman et al.

(10) Patent No.: US 8,263,754 B2
(45) Date of Patent: Sep. 11, 2012

(54) AMPHIPHILES FOR PROTEIN SOLUBILIZATION AND STABILIZATION

(75) Inventors: Samuel Helmer Gellman, Madison, WI (US); Pil Seok Chae, Madison, WI (US); Philip D. Laible, Villa Park, IL (US); Marc J. Wander, Downers Grove, IL (US)

(73) Assignees: Wisconsin Alumni Research Foundation, Madison, WI (US); UChicago Argonne, LLC, Chicago, IL (US)

( * ) Notice: Subject to any disclaimer, the term of this patent is extended or adjusted under 35 U.S.C. 154(b) by 469 days.

(21) Appl. No.: 12/420,701

(22) Filed: Apr. 8, 2009

(65) Prior Publication Data

US 2009/0270598 A1 Oct. 29, 2009

Related U.S. Application Data

(60) Provisional application No. 61/043,273, filed on Apr. 8, 2008.

(51) Int. Cl.
*C07H 15/00* (2006.01)
*A61K 31/7028* (2006.01)

(52) U.S. Cl. ......... 536/17.9; 536/17.2; 536/4.1; 514/25; 530/409

(58) Field of Classification Search ................. 536/17.9, 536/17.2, 4.1; 514/25; 530/409
See application file for complete search history.

(56) References Cited

U.S. PATENT DOCUMENTS 6,172,262 B1 * 1/2001 McQuade et al. ............ 564/182

OTHER PUBLICATIONS

Milkereit et al. (Chemistry and Physics of Lipids (2004), 131(1), 51-61).*
Hansen et al. (Carbohydrate Research 322 (1999) 181-189).*
Chae, P.S., et al., "Glycotripod Amphiphiles for Solubilization and Stabilization of a Membrane-Protein Superassembly: Importance of Branching in the Hydrophillic Portion", *ChemBiochem*, 9, (2008), 1706-1709.
Hjelmeland, L. M., "The Design and Synthesis of Detergents for Membrane Biochemistry", *Methods in Enzymology*, 124, (1986), 135-164.

* cited by examiner

*Primary Examiner* — Shaojia Anna Jiang
*Assistant Examiner* — Michael C Henry
(74) *Attorney, Agent, or Firm* — Clise, Billion & Cyr, P.A.; Michael H. Haukaas

(57) ABSTRACT

The invention provides amphiphiles for manipulating membrane proteins. The amphiphiles can feature carbohydrate-derived hydrophilic groups and branchpoints in the hydrophilic moiety and/or in a lipophilic moiety. Such amphiphiles are useful as detergents for solubilization and stabilization of membrane proteins, including photosynthetic protein superassemblies obtained from bacterial membranes.

22 Claims, 13 Drawing Sheets

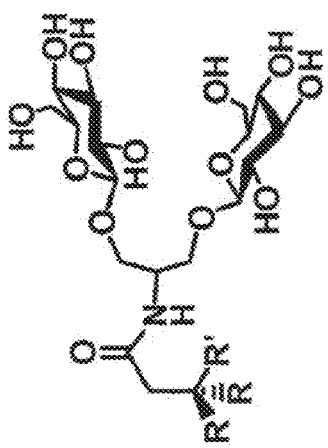

FIG. 14A1

TPA 2 : R = n-Butyl, R' = Phenyl
TPA 21: R = n-Butyl, R' = Cyclohexyl
TPA 25: R = n-Butyl, R' = Isobutyl
TPA 28: R = n-Butyl, R' = p-Iodo-Ph
TPA 29: R = Ethyl, R' = Isobutyl
MPA 2 (C8) : R = H, R' = n-C_8H_{17}
MPA 2 (C10): R = H, R' = n-C_{10}H_{21}
MPA 2 (C12): R = H, R' = n-C_{12}H_{25}
MPA 2 (C14): R = H, R' = n-C_{14}H_{29}
MPA 2 (C16): R = H, R' = n-C_{16}H_{33}
TPA 31 : R = n-Butyl, R' =p-tolyl
TPA 32 : R = n-Butyl, R' = p-(i-Pr)Ph TPA 33 : R = n-Butyl, R' = p-t-Butylphenyl
TPA 34 : R = n-Butyl, R' = p-Biphenyl
TPA 35 : R = n-Pentyl, R' = p-Phenyl
TPA 36 : R = n-Hexyl, R' = p-Phenyl
TPA 45 : R1, R2 = Adamantyl, R' = Butyl
TPA 47 : R =Cyclohexyl, R' = Methyl
TPA 49 : R = Cyclohexyl, R' = Butyl
TPA 50 : R1,R2 =Cyclohexyl, R' = Cyclohexyl
TPA 52 : R1,R2 =Adamantyl, R' = n-Hexyl
TPA 53 : R1,R2 =Cycloheptyl, R' =Cyclohexyl
TPA 54 : R1,R2 =Cyclooctyl, R' =Cyclohexyl
TPA 57 : R =n-Butyl, R' = Cyclopentyl
TPA 73 : R = Cyclohexyl, R' = n-Pentyl

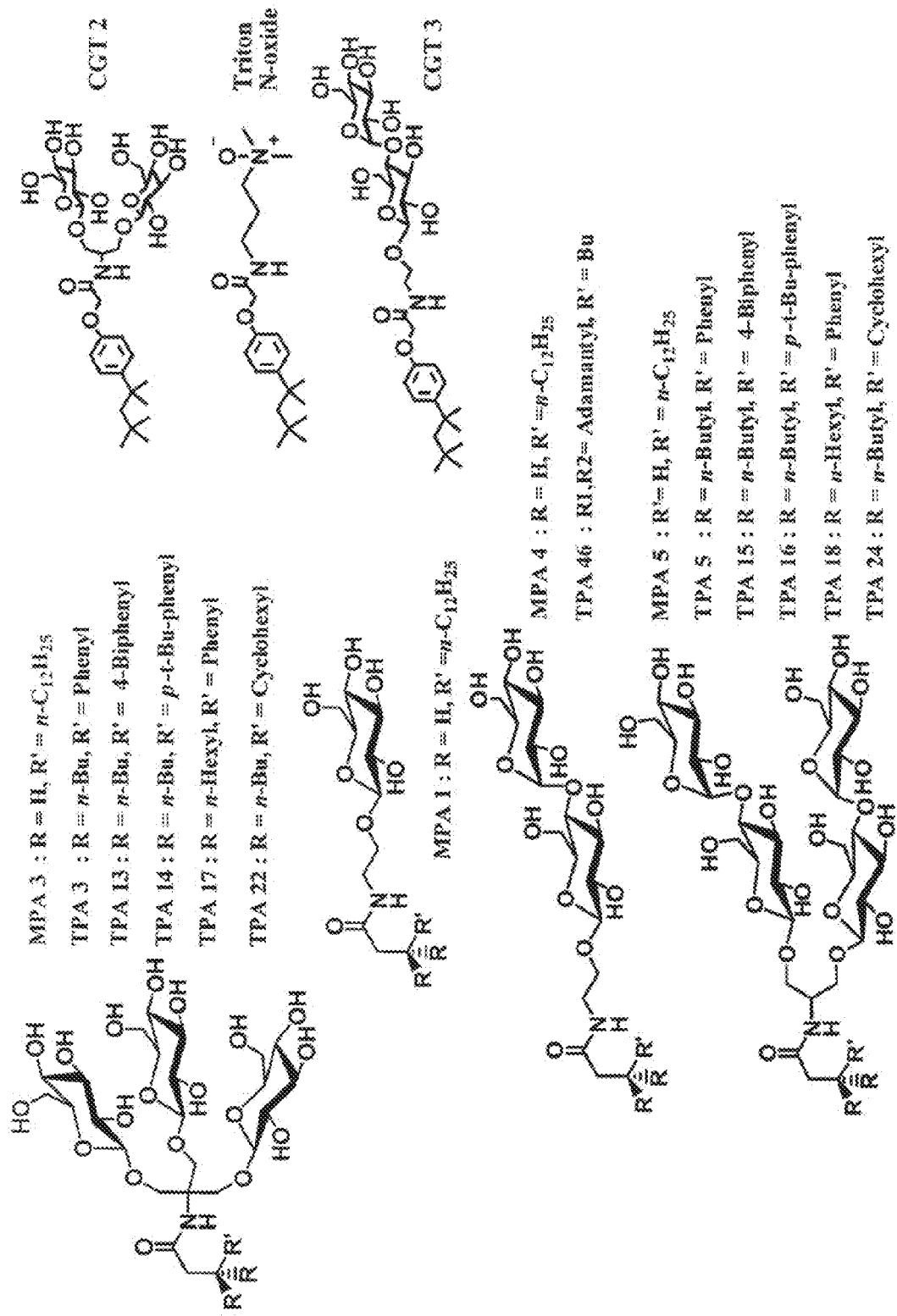
FIG. 14A2

AMPHIPHILES FOR PROTEIN SOLUBILIZATION AND STABILIZATION

RELATED APPLICATIONS

This application claims priority under 35 U.S.C. §119(e) to U.S. Provisional Patent Application No. 61/043,273, filed Apr. 8, 2008, which is incorporated herein by reference.

GOVERNMENT SUPPORT

This invention was made with government support under Grant No. P01 GM75913, awarded by the National Institutes of Health, Contract No. W-31-109-ENG-38, awarded by the Department of Energy, and Contract No. DE-AC02-06CH11357, awarded by the Department of Energy. The United States Government has certain rights in the invention.

BACKGROUND OF THE INVENTION

Isolation and physical characterization of membrane proteins remains a central challenge in biomolecular sciences. Three-dimensional structure determination for membrane proteins, for example, has been successful only within the past two decades, and the set of known membrane protein structures is far smaller than the set of known soluble protein structures. Synthetic amphiphiles, such as detergents, are important tools in this field. They are used to extract embedded proteins from the membranes in which they naturally occur and maintain native protein conformation in the solubilized state. Physical characterization is often carried out with protein-amphiphile complexes, and such complexes are usually the basis for crystallization efforts. Growth of high-quality crystals is typically a rate-limiting step in structure determination. In light of the central role played by synthetic amphiphiles in membrane protein science, surprisingly little effort has been devoted to exploration of non-traditional architectures for these small molecules.

Many available detergents feature a lipophilic segment that is very flexible. This property may facilitate membrane protein solubilization, by allowing detergent molecules to accommodate themselves to lipophilic protein surfaces. However, flexibility could discourage crystallization of a protein-detergent complex, which requires molecular order. A balance between flexibility and rigidity is presumably necessary for maximum utility.

"Tripod amphiphiles," such as Tripod A, were intended to meet the need for new types of synthetic agents that could be used in place of standard detergents for membrane protein manipulation.

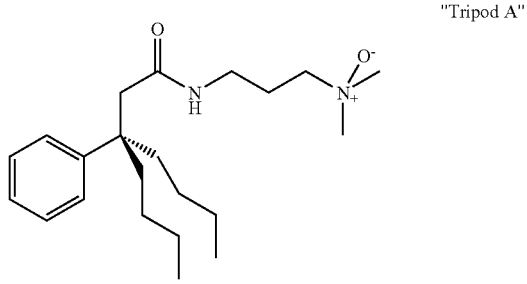
"Tripod A"

The branchpoint in Tripod A imposes partial conformational restriction on the lipophilic segment because torsional motions are limited for bonds near the tetrasubstituted carbon. Both bacteriorhodopsin (bR) and bovine rhodopsin are effectively solubilized by Tripod A, and the resulting protein solutions are stable for several weeks. Two proteins, bR and a potassium channel from *S. lividans*, have been crystallized after solubilization by Tripod A, although no structures have been solved. U.S. Pat. No. 6,172,262 (McQuade et al.), incorporated herein by reference, discloses Tripod A and various related amphiphilic detergents of this general design.

In view of the limited detergents available for solubilization and stabilization of membrane proteins, there exists a need in the field for alternative detergents with expanded, alternate, and/or unique solubilization and protein stabilization properties.

SUMMARY

The invention provides new tools for membrane technology, including effective solubilizing agents and methods for solubilizing, isolating, and characterizing membrane proteins, including intrinsic membrane proteins. The solubilizing agents can include synthetic amphiphiles that exhibit favorable solubilization and stabilization properties in challenging biochemical systems such as, for example, lipid bilayers, photosynthetic superassemblies, and G protein-coupled receptors (GPCRs) such as the beta-2-adrenergic receptor. Accordingly, the invention also provides novel compounds, such as the carbohydrate-based solubilizing agents described herein, for use in manipulating membrane proteins. Thus, the invention is directed to synthetic amphiphiles that can display favorable solubilization and stabilization properties in challenging biochemical systems.

Accordingly, in a first aspect the invention encompasses an amphiphilic compound of Formula I:

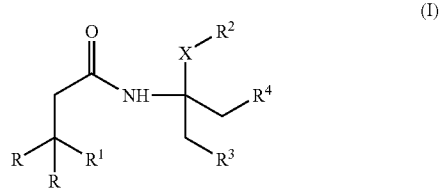

(I)

wherein each R is independently H, $C_1$-$C_{16}$ straight or branched alkyl, $C_3$-$C_8$ cycloalkyl, $C_3$-$C_8$ cycloalkenyl, phenyl, biphenyl, or $C_3$-$C_8$ cycloalkyl, $C_3$-$C_8$ cycloalkenyl, phenyl, biphenyl substituted with one, two, or three $C_1$-$C_6$ straight or branched alkyl groups; or the two R groups together with the carbon to which they are attached form a $C_3$-$C_8$ cycloalkyl, a $C_3$-$C_8$ cycloalkenyl, or an adamantyl ring system;

$R^1$ is $C_1$-$C_{16}$ straight or branched alkyl, $C_3$-$C_8$ cycloalkyl, $C_3$-$C_8$ cycloalkenyl, phenyl, biphenyl, halophenyl, p-tolyl, adamantyl or $C_3$-$C_8$ cycloalkyl, $C_3$-$C_8$ cycloalkenyl, phenyl, biphenyl, halophenyl, p-tolyl, adamantyl substituted with one, two, or three $C_1$-$C_6$ straight or branched alkyl groups; or R, R, and $R^1$ together with the carbon to which they are attached form an adamantyl ring system, optionally substituted with one, two, or three $C_1$-$C_6$ straight or branched alkyl groups;

X is $CH_2$ or a direct bond;

$R^2$ is H, an O-linked $C_6$ glycosyl residue, or an O-linked oligosaccharide comprising two or more glycosyl residues;

$R^3$ is an O-linked $C_6$ glycosyl residue, or an O-linked oligosaccharide comprising two or more glycosyl residues, or a $C_1$-$C_4$ alkyl-(N,N-dimethyl)N-oxide; and $R^4$ is an O-linked $C_6$ glycosyl residue, an O-linked oligosaccharide comprising two or more glycosyl residues, or a $C_1$-$C_4$ alkyl-(N,N-dimethyl)N-oxide.

In one embodiment, each R is independently H, ethyl, n-propyl, n-butyl, n-pentyl, n-hexyl, n-heptyl, adamantyl, cyclopentyl, cyclohexyl, cycloheptyl, or cyclooctyl. $R^1$ can be $C_1$-$C_{16}$ n-alkyl, isobutyl, cyclopentyl, cyclohexyl, cycloheptyl, cyclooctyl, phenyl, halophenyl, p-tolyl, p-isopropyl phenyl, p-t-butylphenyl, or p-biphenyl.

In another embodiment, each R is n-butyl and $R^1$ is phenyl; each R is n-butyl and $R^1$ is cyclohexyl; each R is n-butyl and $R^1$ is isobutyl; each R is n-butyl and $R^1$ is p-iodophenyl; each R is ethyl and $R^1$ is isobutyl; each R is n-butyl and $R^1$ is p-tolyl; each R is n-butyl and $R^1$ is p-isopropyl phenyl; each R is n-butyl and $R^1$ is p-t-butyl phenyl; each R is n-pentyl and $R^1$ is phenyl; or each R is n-hexyl and $R^1$ is phenyl.

In one embodiment, the compound of Formula I is a compound of Formula II:

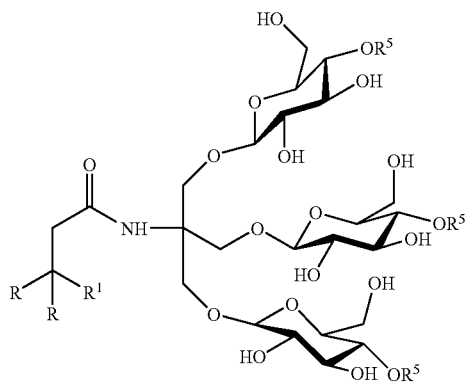

wherein R and $R^1$ are as defined for Formula I, and $R^5$ is H or a $C_6$ glycosyl residue.

In one embodiment, X is a direct bond and $R^2$ is H. In another embodiment, the compound of Formula I is a compound of Formula III:

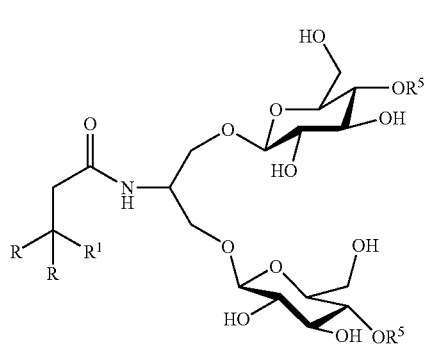

(III)

wherein R and $R^1$ are as defined for Formula I, and $R^5$ is H or a $C_6$ glycosyl residue.

In some embodiments, one or both of $R^3$ and $R^4$ are O-linked glucose, mannose, galactose, maltose or sucrose residues. In other embodiments, one or both of $R^3$ and $R^4$ are $C_1$-$C_4$ alkyl-(N,N-dimethyl)N-oxide.

In another aspect the invention encompasses an amphiphilic compound of Formula IV:

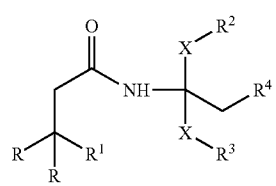

(IV)

wherein both R groups are H, or one R is H and the other R is $C_1$-$C_{16}$ straight or branched alkyl, $C_3$-$C_8$ cycloalkyl, $C_3$-$C_8$ cycloalkenyl, phenyl, biphenyl, or $C_3$-$C_8$ cycloalkyl, $C_3$-$C_8$ cycloalkenyl, phenyl, biphenyl substituted with one, two, or three $C_1$-$C_6$ straight or branched alkyl groups; or the two R groups together with the carbon to which they are attached form an adamantyl ring system;

$R^1$ is $C_1$-$C_{16}$ straight or branched alkyl, $C_3$-$C_8$ cycloalkyl, $C_3$-$C_8$ cycloalkenyl, phenyl, biphenyl, halophenyl, p-tolyl, adamantyl or $C_3$-$C_8$ cycloalkyl, $C_3$-$C_8$ cycloalkenyl, phenyl, biphenyl, halophenyl, p-tolyl, adamantyl substituted with one, two, or three $C_1$-$C_6$ straight or branched alkyl groups; or R, R, and $R^1$ together with the carbon to which they are attached form an adamantyl ring system, optionally substituted with one, two, or three $C_1$-$C_6$ straight or branched alkyl groups;

each X is independently $CH_2$ or a direct bond;

$R^2$ is H, an O-linked $C_6$ glycosyl residue, or an O-linked oligosaccharide comprising two or more glycosyl residues;

$R^3$ is H, an O-linked $C_6$ glycosyl residue, or an O-linked oligosaccharide comprising two or more glycosyl residues, or a $C_1$-$C_4$ alkyl-(N,N-dimethyl)N-oxide; and $R^4$ is an O-linked $C_6$ glycosyl residue, an O-linked oligosaccharide comprising two or more glycosyl residues, or a $C_1$-$C_4$ alkyl-(N,N-dimethyl)N-oxide.

In one embodiment, each R is independently H, ethyl, n-propyl, n-butyl, n-pentyl, n-hexyl, n-heptyl, adamantyl, cyclopentyl, cyclohexyl, cycloheptyl, or cyclooctyl; and $R^1$ is $C_1$-$C_{16}$ n-alkyl, isobutyl, cyclopentyl, cyclohexyl, cycloheptyl, cyclooctyl, phenyl, halophenyl, p-tolyl, p-isopropyl phenyl, p-t-butylphenyl, or p-biphenyl.

In some embodiments, each X is a direct bond, and $R^2$ and $R^3$ are both H. In some embodiments, $R^4$ is a $C_1$-$C_4$ alkyl-(N,N-dimethyl)N-oxide. In other embodiments, $R^4$ is an O-linked $C_6$ glycosyl residue, optionally substituted by a second O-linked glycosyl residue.

In certain specific embodiments, the compound of Formula IV is:

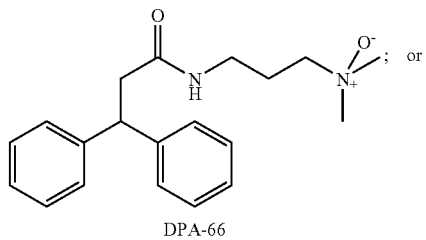

DPA-66

-continued

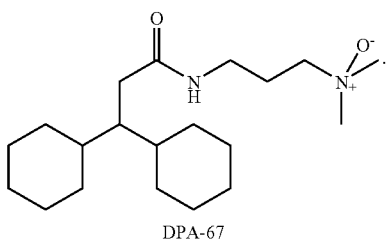
DPA-67

In some embodiments, the two R groups together with the carbon to which they are attached form an adamantyl ring system; $R^1$ is a $C_1$-$C_{16}$ straight or branched alkyl; —X—$R^2$ is direct bond-H; —X—$R^3$ is direct bond-H or —CH$_2$—O-linked $C_6$ glycosyl residue or O-linked oligosaccharide comprising two or more glycosyl residues. In certain specific embodiments, the compound of Formula IV is:

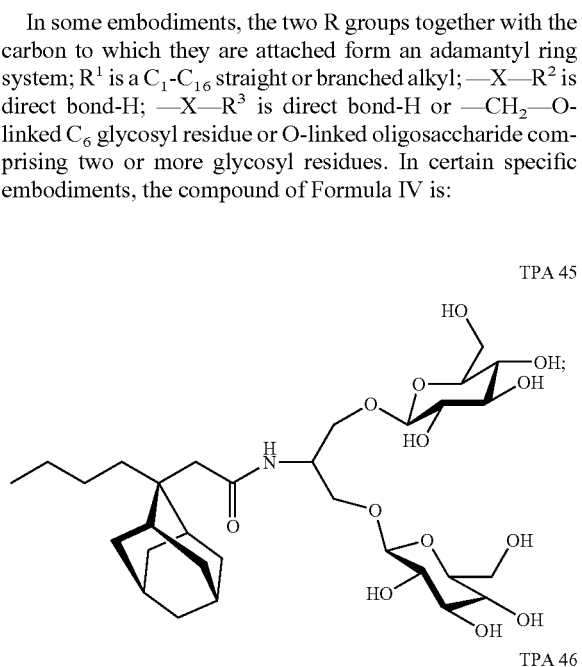

TPA 45

TPA 46

TPA 52

In other embodiments, the compound of Formula IV is a compound of Formula IV-A:

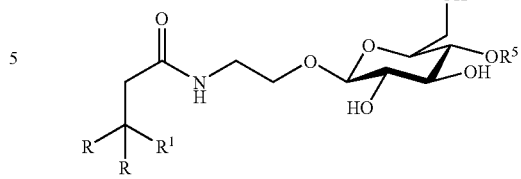

(IV-A)

wherein R and $R^1$ are as defined for Formula IV, and $R^5$ is H or a $C_6$ glycosyl residue. In certain specific embodiments, the compound of Formula IV-A is:

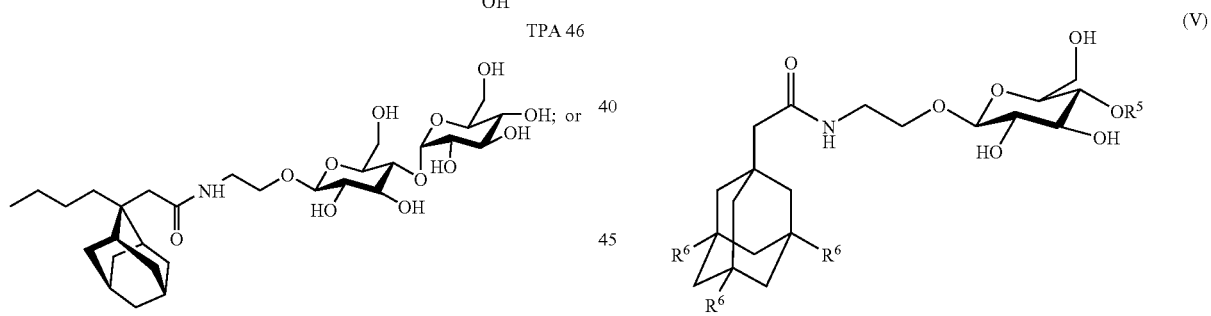

wherein $R^5$ is H or a $C_6$ glycosyl residue. In another embodiment, the compound of Formula IV-A can be a compound of Formula V:

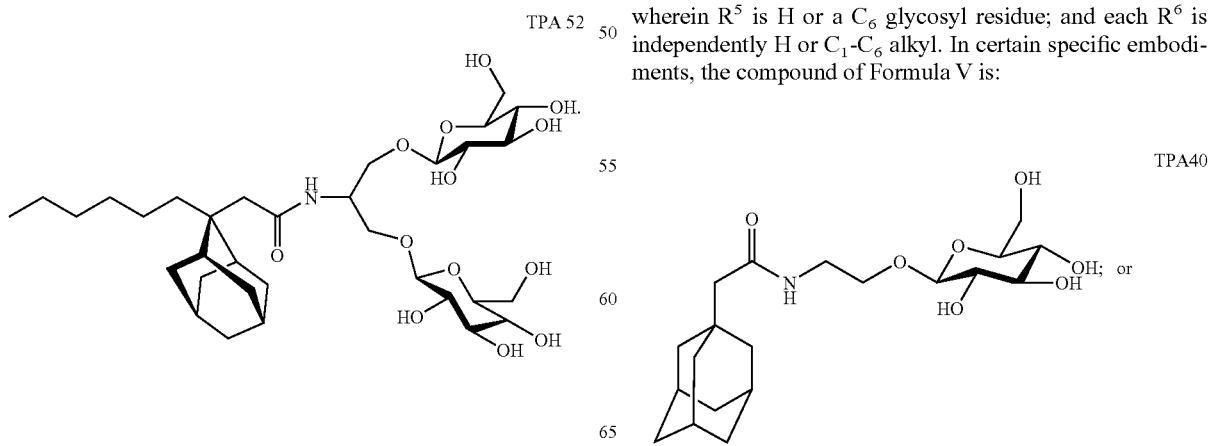

(V)

TPA40 wherein $R^5$ is H or a $C_6$ glycosyl residue; and each $R^6$ is independently H or $C_1$-$C_6$ alkyl. In certain specific embodiments, the compound of Formula V is:

-continued

TPA44

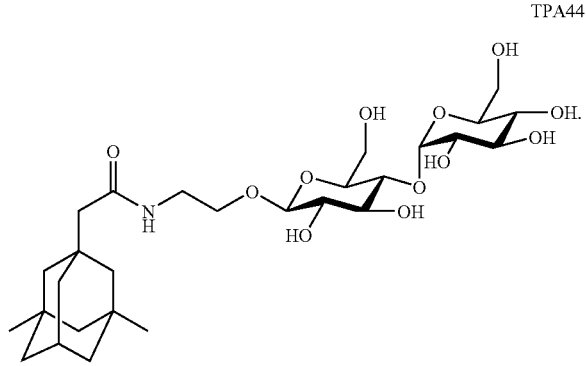

In another aspect the invention encompasses an amphiphilic compound of Formula VI:

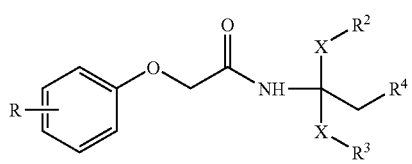

(VI)

wherein R is H, $C_1$-$C_{16}$ straight or branched alkyl, $C_3$-$C_8$ cycloalkyl, $C_3$-$C_8$ cycloalkenyl, phenyl, biphenyl, or $C_3$-$C_8$ cycloalkyl, $C_3$-$C_8$ cycloalkenyl, phenyl, biphenyl substituted with one, two, or three $C_1$-$C_6$ straight or branched alkyl groups;

each X is independently $CH_2$ or a direct bond;

$R^2$ is H, an O-linked $C_6$ glycosyl residue, or an O-linked oligosaccharide comprising two or more glycosyl residues;

$R^3$ is H, an O-linked $C_6$ glycosyl residue, or an O-linked oligosaccharide comprising two or more glycosyl residues, or a $C_1$-$C_4$ alkyl-(N,N-dimethyl)N-oxide; and $R^4$ is an O-linked $C_6$ glycosyl residue, an O-linked oligosaccharide comprising two or more glycosyl residues, or a $C_1$-$C_4$ alkyl-(N,N-dimethyl)N-oxide.

In one embodiment, R is a $C_3$-$C_{10}$ branched alkyl. In some embodiments, —X—$R^2$ is direct bond-H; —X—$R^3$ is direct bond-H or —$CH_2$—O-linked $C_6$ glycosyl residue or O-linked oligosaccharide comprising two or more glycosyl residues; and $R^4$ is O-linked $C_6$ glycosyl residue or O-linked oligosaccharide comprising two or more glycosyl residues, or a $C_1$-$C_4$ alkyl-(N,N-dimethyl)N-oxide. In certain specific embodiments, the compound of Formula VI is

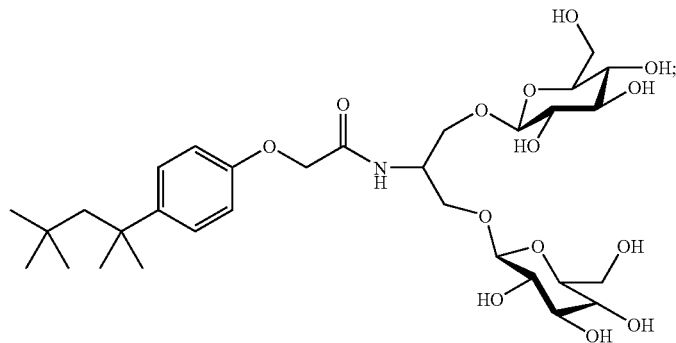

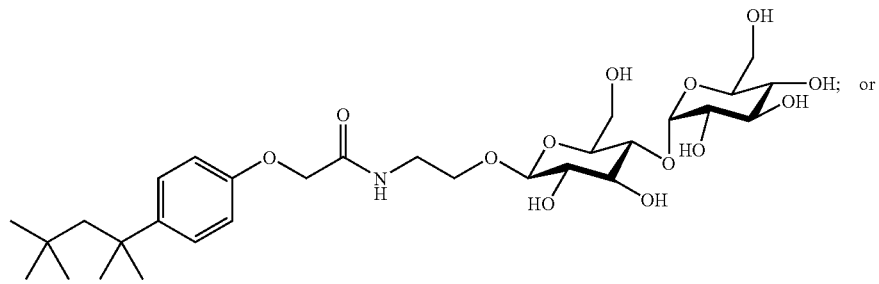

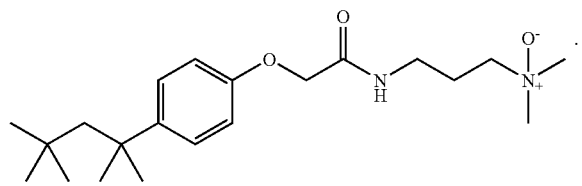

In another aspect the invention provides compounds of Formula VII:

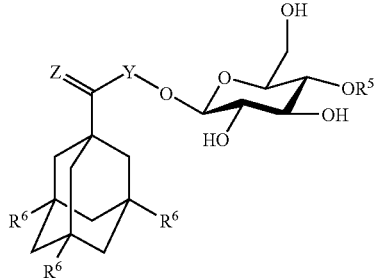
(VII)

wherein

Y is CH$_2$, —NH(C$_1$-C$_4$ alkyl)-, or a direct bond;
Z is O or absent;
R$^5$ is H or a C$_6$ glycosyl residue; and
each R$^6$ is independently H or C$_1$-C$_6$ alkyl.

In some embodiments, Y is CH$_2$ or —NH(CH$_2$—CH$_2$)—. In other embodiments, Y is a direct bond. In some embodiments, Z is O. In other embodiments, Z is absent (e.g., the two bonds to Z are attached to two separate H atoms). In some embodiments, R$^5$ is H. In other embodiments, R$^5$ is an O-linked glucose, mannose, galactose. In certain specific embodiments, the compound of Formula VII is:

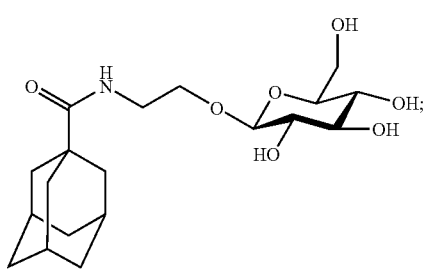
TPA41

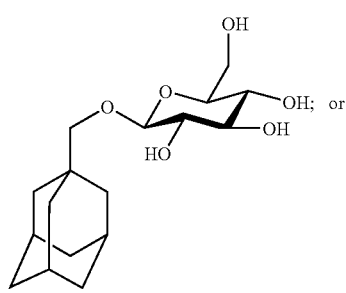
TPA42

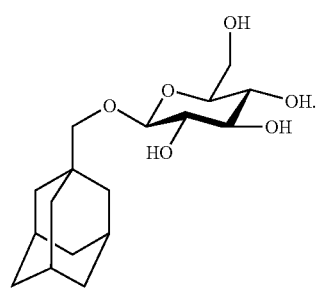
TPA43

In another aspect the invention provides compounds of Formula VIII:

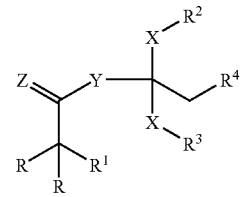
(VIII)

wherein

Y is C$_1$-C$_4$ alkylene, —NH(C$_1$-C$_4$ alkyl)-, or a direct bond;
Z is O or absent;
each R is independently C$_1$-C$_{16}$ straight or branched alkyl, C$_3$-C$_8$ cycloalkyl, C$_3$-C$_8$ cycloalkenyl, phenyl, biphenyl, or C$_3$-C$_8$ cycloalkyl, C$_3$-C$_8$ cycloalkenyl, phenyl, biphenyl substituted with one, two, or three C$_1$-C$_6$ straight or branched alkyl groups; or the two R groups together with the carbon to which they are attached form a C$_3$-C$_8$ cycloalkyl, a C$_3$-C$_8$ cycloalkenyl, or an adamantyl ring system;

R$^1$ is H, C$_1$-C$_{16}$ straight or branched alkyl, C$_3$-C$_8$ cycloalkyl, C$_3$-C$_8$ cycloalkenyl, phenyl, biphenyl, halophenyl, p-tolyl, adamantyl or C$_3$-C$_8$ cycloalkyl, C$_3$-C$_8$ cycloalkenyl, phenyl, biphenyl, halophenyl, p-tolyl, adamantyl substituted with one, two, or three C$_1$-C$_6$ straight or branched alkyl groups; or R, R, and R$^1$ together with the carbon to which they are attached form an adamantyl ring system, optionally substituted with one, two, or three C$_1$-C$_6$ straight or branched alkyl groups;

each X is independently CH$_2$ or a direct bond;

R$^2$ is H, an O-linked C$_6$ glycosyl residue, an O-linked oligosaccharide comprising two or more glycosyl residues, or a C$_1$-C$_4$ alkyl-(N,N-dimethyl)N-oxide;

R$^3$ is H, an O-linked C$_6$ glycosyl residue, an O-linked oligosaccharide comprising two or more glycosyl residues, or a C$_1$-C$_4$ alkyl-(N,N-dimethyl)N-oxide; and R$^4$ is an O-linked C$_6$ glycosyl residue, an O-linked oligosaccharide comprising two or more glycosyl residues, or a C$_1$-C$_4$ alkyl-(N,N-dimethyl)N-oxide.

In some embodiments, Y is CH$_2$, both R groups are C$_1$-C$_8$ straight chain alkyl, R$^1$ is phenyl, —X—R$^2$ is direct bond-H, and one or both of R$^3$ and R$^4$ are O-linked glucose, mannose, galactose, maltose or sucrose residues. In other embodiments, one or both of R$^3$ and R$^4$ are C$_1$-C$_4$ alkyl-(N,N-dimethyl)N-oxide. In certain specific embodiments, the compound of Formula VIII is:

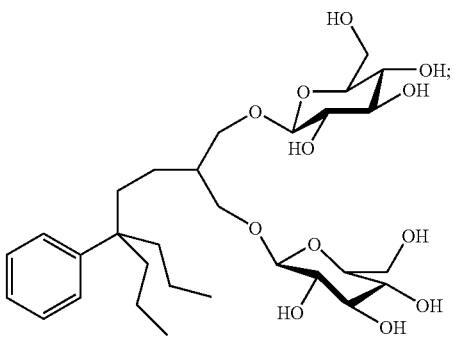

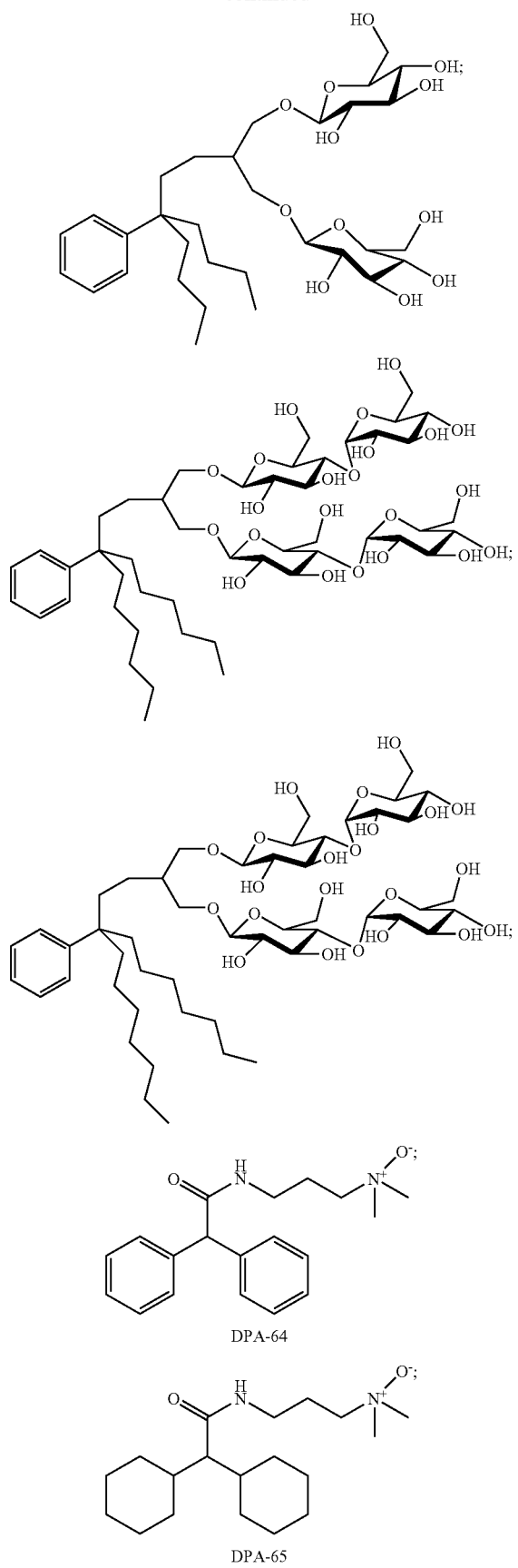

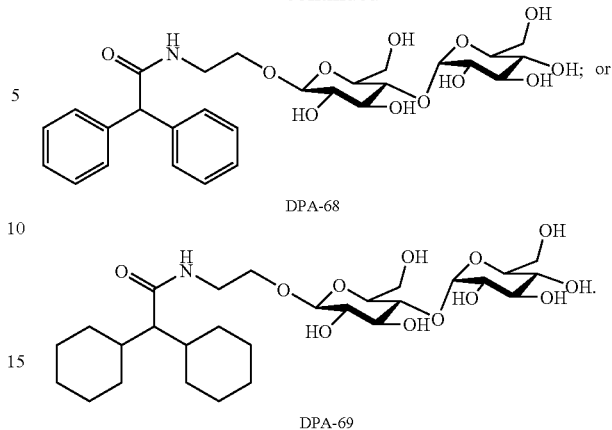

Specific amphiphilic compounds of Formulas I-VIII include the specific compounds illustrated in FIGS. 14A and 14B, for example, those designated TPA2, TPA21 (also referred to as "TPA-2-S" herein), TPA25, TPA29, TPA31, TPA32, TPA33, TPA35, TPA36. It is also important to note that in some embodiments, the values of variable groups of one Formula (e.g., R, $R^1$, $R^2$, $R^3$, $R^4$, $R^5$, $R^6$, X, Y, or Z) can be specifically included in or excluded from that same variable in another Formula, to provide other embodiments of the invention.

The invention provides compositions that include a plurality of an amphiphilic compound as described herein, e.g., a compound of any one of Formulas I-VIII, and a membrane protein. Such compositions can take the form of micelles, formed from a plurality amphiphilic compounds as described herein, optionally in conjunction with one or more other micelle-forming compounds, where the plurality of compounds surround a membrane protein.

The invention also provides methods for manipulating membrane proteins. For example, a method is provided for solubilizing a membrane protein by contacting the protein in an aqueous environment with an effective amount of a compound as described herein, and optionally heating the protein and the compound, to provide the solubilized protein encapsulated in micelles of the compound. The effective amount of the compound can be an amount of the compound necessary to achieve its critical micelle concentration, to about 10 times, about 100 times, about 1,000 times, or about 10,000 times, the amount of the compound necessary to achieve its critical micelle concentration. The method can also include employing a buffer, a second amphiphile or detergent, or other reagents, in the aqueous environment to aid in the solubilization and stabilization of membrane proteins.

The invention also provides a method of purifying a membrane protein by contacting the protein in an aqueous environment with an effective amount of a compound as described herein, to form micelles comprising a plurality of the compounds surrounding the protein, and isolating the micelles, to provide the purified membrane protein encapsulated in micelles of the compound. Other techniques for using the amphiphilic compounds described herein include techniques for stabilizing, crystallizing, and/or characterizing a protein while in a detergent micelle made up of a compound described herein.

The invention has several advantages over previous technologies, including previously reported tripod amphiphiles. For example, the amphiphilic compounds TPA2 and TPA-2-S, as well as others, exhibit superior membrane protein solubilization and, surprisingly, stabilization properties, as compared to a wide variety of known detergents. Furthermore, many of the amphiphiles described herein do not include aromatic groups, therefore they are highly suitable for "optical" characterization methods such as UV absorbance spectroscopy and UV circular dichroism, when characterizing a protein solubilized by such amphiphiles.

Other uses of the amphiphiles described herein include their use as end caps in bicelle formulations, amphiphilic additions in crystallization trials, components of detergent mixtures, stabilizing factors in functional assays, detergents in exchange schemes, solubilization agents in cell-free expression reactions, as well as their use for separation on polyacrylamide gels using native protocols to maintain native states, for use in sample buffers on membrane fractions used to solubilize membrane proteins and to prepare proteins for separation on gels, and for use with Bug Buster® Protein Extraction Reagent formulations designed to break open cells and survey protein present, for example, without using sonication and/or lysozyme treatment and osmotic shock, such as with eukaryotic cell pellets that are relatively fragile and easily disrupted. Other objects, features and advantages of the present invention will become apparent from the following description, claims and drawings.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention, however, one skilled in the art will understand that portions of the example or aspect may be used in combination with other examples or aspects of the invention.

FIG. 2 is redrawn using a much smaller and finer scale to focus on the spectra of solubilized protein complexes extracted from membranes of R. capsulatus using these two amphiphiles.

As seen in FIG. 6, the use of the diglucoside variant (MPA-2) results far greater yield, in comparison to the triglucoside and dimaltoside variants (MPA-3 and MPA-5, respectively).

FIGS. 14A and 14B. Chemical structures of amphiphilic compounds of the invention, including several subjected to the assay described in Example 2. The label "R1, R2" indicates that two alkyl ("R") groups are linked each other to form the recited ring.

DETAILED DESCRIPTION

Figure 1:
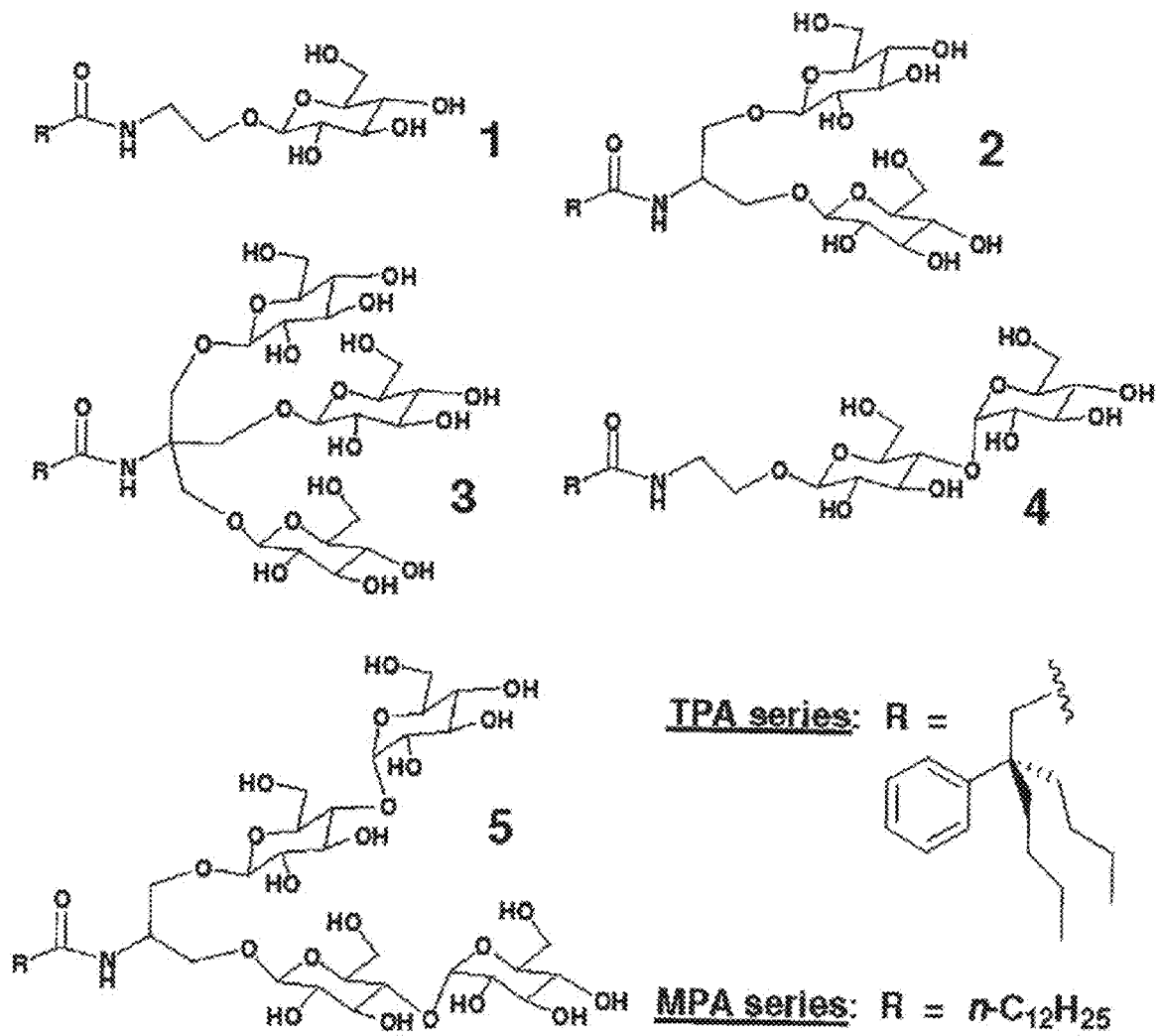
FIG. 1. Chemical structures of tripod amphiphiles TPA-1 to TPA-5 and their monopod analogues MPA-1 to MPA-5.

Many integral membrane proteins are not stable in the presence of detergents. Therefore, there is a need for new synthetic detergents that can maintain the native state of integral membrane proteins long enough for structural studies and characterization. Several non-classical amphiphiles has been reported for this purpose, however those amphiphiles typically have not provided improved behavior relative to dodecyl-β-$_D$-maltopyranoside (DDM) in terms of membrane protein stabilization. Compounds disclosed herein provide answers to the need for new synthetic detergents with advantageous properties.

Some of the new amphiphiles disclosed herein are mild enough to maintain a membrane protein stable, for example, for a longer period of time than DDM, or for at least about two weeks. The properties of these amphiphiles can be fine-tuned by employing a variety of the hydrophobic groups, for example, of different carbon lengths and structural arrangements, such as in straight or branched alkyl groups, cycloalkyl groups, or aryl groups, and a variety of hydrophilic groups, for example, monosaccharides, disaccharides, or alkyl dimethyl N-oxides.

A variety of known biochemical detergents have been used in manipulating various types of membrane proteins, including decylmaltoside (DM), dodecylmaltoside (DDM), octyl glucoside (OG), nonylglucoside (NG), and lauryldimethylamine oxide (LDAO). Detergents such as LDAO and OG are considered to be rather harsh detergents. They form small compact micelles in solution and have been used to crystallize some proteins. The crystallization process may have been aided by the formation of small sized protein-detergent complexes. However, these detergents are not effective at maintaining the native state of many membrane proteins, which tend to denature and form irreversible aggregates.

DDM is considered a milder detergent than LDAO and OG. It has been found to be more effective at maintaining the native states of integral membrane proteins in solution. However, DDM forms relatively large micelles, resulting in large protein-detergent complexes. A protein in a large protein-detergent complex is a less than ideal condition for obtaining effective results in NMR studies and crystallization trials.

Accordingly, new amphiphiles are sought that have more ideal properties for solubilization, isolation, purification, stabilization, crystallization, and/or structural determination of membrane proteins, including intrinsic membrane proteins. Such amphiphiles should form small micelles, which result in small membrane-protein complexes. For certain purposes, the detergent strength of the amphiphiles should be relatively mild, thereby allowing for the maintenance of the native structure of membrane proteins with little or no denaturing. The amphiphiles described herein are provided to meet these needs.

New detergents described herein have been evaluated with an *R. capsulatus* photosynthetic superassembly solubilization assay. The assay was previously used to evaluate OG and DDM, as well as numerous other commercial detergents. Many detergents described herein were found to be sufficiently mild such that they maintain several membrane proteins substantially in their native conformations, without significant degradation of the protein compared to, for example, DDM, one of the mildest known classical detergents.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the invention, which is limited only by the appended claims.

Definitions

Unless defined otherwise, all technical and scientific terms used herein have the same meanings as commonly understood by one of ordinary skill in the art. Although any methods and materials similar or equivalent to those described herein can be used in the practice or testing of the invention, the preferred methods and materials are now described.

As used herein, certain terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

The term "and/or" means any one of the items, any combination of the items, or all of the items with which this term is associated.

As used herein and in the appended claims, the singular forms "a", "an", and "the" include plural reference unless the context dictates otherwise. Thus, for example, a reference to "a compound" includes a plurality of such compounds, so that a compound X includes a plurality of compounds X. As well, the terms "a" (or "an"), "one or more" and "at least one" can be used interchangeably herein. It is also to be noted that the terms "comprising", "including", and "having" can be used interchangeably.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer. Unless indicated otherwise herein, the term "about" is intended to include values, e.g., weight percents, proximate to the recited range that are equivalent in terms of the functionality of the individual ingredient, the composition, or the embodiment. In addition, unless indicated otherwise herein, a recited range (e.g., weight percents or carbon groups) includes each specific value, integer, decimal, or identity within the range.

The phrase "one or more" is readily understood by one of skill in the art, particularly when read in context of its usage. For example, one or more substituents on a phenyl ring refers to one to five, or one to up to four, for example if the phenyl ring is disubstituted.

The term "contacting" refers to the act of touching, making contact, or of bringing to immediate or close proximity, including at the molecular level, for example, to bring about a chemical reaction or physical change, e.g., in a solution or other reaction mixture.

An "effective amount" generally means an amount which provides the desired effect.

The term "alkyl" refers to a branched or unbranched hydrocarbon having, for example, from 1 to 20 carbon atoms, and often 1 to about 12, about 1 to 8 carbons, or 1 to about 6 carbon atoms. Examples include, but are not limited to, methyl, ethyl, 1-propyl, 2-propyl, 1-butyl, 2-methyl-1-propyl, 2-butyl, 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted with 1, 2, 3, 4, 5, 6, 7, 8, 9, or 10 substituents. For example, a substituted alkyl group can be a haloalkyl group, e.g., an alkyl group substituted with one or more halo groups as described below for the term substituted, or the alkyl can be substituted with a aryl group, to form an (aryl)alkyl group, in some embodiments. The alkyl can also be optionally partially or fully unsaturated. As such, the recitation of an alkyl group can include both alkenyl and alkynyl groups. The alkyl can be a monovalent hydrocarbon radical, as described and exemplified above, or it can be a divalent hydrocarbon radical (i.e., alkylene), according to the context of its usage. Additionally, the alkyl group can be optionally interrupted, as described below for the term interrupted.

As used herein, when a group or moiety can be substituted, the term "substituted" indicates that one or more (e.g., 1, 2, 3, 4, 5, or 6; in some embodiments 1, 2, or 3; and in other embodiments 1 or 2) hydrogens on the "substituted" group can be replaced with one or more of a selection of recited groups or with a suitable group known to those of skill in the art (e.g., one or more of the groups recited below), provided that the indicated atom's normal valency is not exceeded, and that the substitution results in a stable compound. Suitable substituents of a substituted group can include one or more of alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acetylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl (alkyl)amine, and cyano. Additionally, the suitable substituent groups can include, e.g., —X, —R, —O$^-$, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, NC(=O)R, —C(=O)R, —C(=O)NRR—S(=O)$_2$O$^-$, —S(=O)$_2$OH, —S(=O)$_2$R, —OS(=O)$_2$OR, —S(=O)$_2$NR, —S(=O)R, —OP(=O)O$_2$RR, —P(=O)O$_2$RR, —P(=O)(O$^-$)$_2$, —P(=O)(OH)$_2$, —C(=O)R, —C(=O)X, —C(S)R, —C(O)OR, —C(O)O$^-$, —C(S)OR, —C(O)SR, —C(S)SR, —C(O)NRR, —C(S)NRR, —C(NR)NRR, where each X is independently a halogen ("halo"): F, Cl, Br, or I; and each R is independently H, alkyl, aryl, heteroaryl, heterocycle, a protecting group or prodrug moiety. As would be readily understood by one skilled in the art, when a substituent is keto (=O) or thioxo (=S), or the like, then two hydrogen atoms on the substituted atom are replaced. Any one or more of the above substituents can also be specifically excluded from a given embodiment.

The term "interrupted" indicates that another group is inserted between two adjacent carbon atoms (and the hydrogen atoms to which they are attached (e.g., methyl (CH$_3$), methylene (CH$_2$) or methine (CH))) of a particular carbon chain being referred to in the expression using the term "interrupted", provided that each of the indicated atoms' normal valency is not exceeded and the interruption results in a stable compound. Suitable groups that can interrupt a carbon chain include, e.g., one or more non-peroxide oxy (—O—), thio (—S—), imino (—N(H)—), methylene dioxy (—OCH$_2$O—), carbonyl (—C(=O)—), carboxy (—C(=O)O—), carbonyldioxy (—OC(=O)O—), carboxylato (—OC(=O)—), imine (C=NH), sulfinyl (SO) or sulfonyl (SO$_2$) groups, or a combination thereof. Alkyl groups can be interrupted by one or more (e.g., 1, 2, 3, 4, 5, or about 6) of the aforementioned suitable groups. The site of interruption can also be between a carbon atom of an alkyl group and a carbon atom to which the alkyl group is attached.

The term "alkenyl" refers to a monoradical branched or unbranched partially unsaturated hydrocarbon chain (i.e. a carbon-carbon, sp$^2$ double bond). In one embodiment, an alkenyl group can have from 2 to 10 carbon atoms, or 2 to 6 carbon atoms. In another embodiment, the alkenyl group has from 2 to 4 carbon atoms. Examples include, but are not limited to, ethylene or vinyl, allyl, cyclopentenyl, 5-hexenyl, and the like. The alkenyl can be unsubstituted or substituted.

The term "alkynyl" refers to a monoradical branched or unbranched hydrocarbon chain, having a point of complete unsaturation (i.e. a carbon-carbon, sp triple bond). In one embodiment, the alkynyl group can have from 2 to 10 carbon atoms, or 2 to 6 carbon atoms. In another embodiment, the alkynyl group can have from 2 to 4 carbon atoms. This term is exemplified by groups such as ethynyl, 1-propynyl, 2-propynyl, 1-butynyl, 2-butynyl, 3-butynyl, 1-hexynyl, 2-hexynyl, 3-hexynyl, 1-octynyl, and the like. The alkynyl can be unsubstituted or substituted.

The term "cycloalkyl" refers to cyclic alkyl groups of from 3 to about 20 carbon atoms having a single cyclic ring or multiple condensed rings. Many cycloalkyl typically include about 3-12 carbon atoms, or about 3-8 carbon atoms. Cycloalkyl groups include, by way of example, single ring structures such as cyclopropyl, cyclobutyl, cyclopentyl, cyclooctyl, and the like, or multiple ring structures such as adamantanyl, and the like. The cycloalkyl can be unsubstituted or substituted. The cycloalkyl group can be monovalent or divalent, and can be optionally substituted as described above for alkyl groups. The cycloalkyl group can optionally include one or more cites of unsaturation, for example, the cycloalkyl group can include one or more carbon-carbon double bonds, such as, for example, cyclohexene, 1,3-cyclohexadiene, 1,4-cyclohexadiene, and the like. The cycloalkyl group can be a carbocycle, which refers to a saturated or partially unsaturated ring having 3 to 8 carbon atoms as a monocycle, 7 to 12 carbon atoms as a bicycle, and up to about 20 carbon atoms as a polycycle. Monocyclic carbocycles typically have 3 to 6 ring atoms, still more typically 5 or 6 ring atoms. Bicyclic carbocycles can have 7 to 12 ring atoms, e.g., arranged as a bicyclo [4,5], [5,5], [5,6] or [6,6] system, or 9 or 10 ring atoms arranged as a bicyclo[5,6] or [6,6] system. Examples of carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, or 1-cyclohex-3-enyl. The carbocycle can be optionally substituted as described above for alkyl groups.

The term "alkoxy" refers to the group alkyl-O—, where alkyl is as defined herein. In one embodiment, alkoxy groups include, e.g., methoxy, ethoxy, n-propoxy, iso-propoxy, n-butoxy, tert-butoxy, sec-butoxy, n-pentoxy, n-hexyloxy, 1,2-dimethylbutoxy, and the like. The alkoxy can be unsubstituted or substituted.

As used herein, "aryl" refers to an aromatic hydrocarbon group derived from the removal of one hydrogen atom from a single carbon atom of a parent aromatic ring system. The radical can be at a saturated or unsaturated carbon atom of the parent ring system. The aryl group can have 6-18 carbon atoms, 6-14 carbon atoms, or 6-10 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described above for alkyl groups. For example, an aryl group can be substituted with one or more substituents (as described above) to provide various substituted aryls, such as pentafluorophenyl or para-trifluoromethylphenyl, and the like, as well as halophenyl groups, which can be substituted by one to five halo groups, and each halo group can be independently fluoro, chloro, bromo, or iodo.

The term "halo" refers to the groups fluoro, chloro, bromo, and iodo. Similarly, the term "halogen" refers to fluorine, chlorine, bromine, and iodine.

As to any of the above groups, which contain one or more substituents, it is understood, of course, that such groups do not contain any substitution or substitution patterns that are sterically impractical and/or synthetically non-feasible. In addition, the compounds of this invention include all stereochemical isomers arising from the substitution of these compounds, including diasteriomers.

The term "O-linked $C_6$ glycosyl residue" refers to a six carbon sugar, which can in some embodiments, be substituted with a second O-linked $C_6$ glycosyl residue to form a saccharide dimer. The O-linked $C_6$ glycosyl residue include amino sugars such as glucamine or gluconic acid derivatives (e.g., —$CH_2(CHOH)_4$—$CH_2OH$ and —$C(=O)(CHOH)_4$—$CH_2OH$, respectively). Six carbon sugars and dimers thereof can be referred to as monosaccharides or disaccharides, respectively. A saccharide group is a type of polar group ("$P^1$ or $P^2$,"), which can be a substituent of another group, formula, or molecule. The O-linked $C_6$ glycosyl residue can be a monosaccharide such as such as allose, altrose, glucose, mannose, gulose, idose, galactose, or talose, optionally substituted to form a disaccharide such as maltose, galactose, or sucrose, or an amino or amide derivative thereof the monosaccharide or disaccharide. The saccharide groups can also be in pyranose form, or linear form.

The term "buffer" refers to a compound or mixtures of compounds that, by their presence in solution, resist changes in pH upon the addition of small quantities of acid or alkali. A combination of a weak acid and its conjugate base (i.e., its salt) or a weak base and its conjugate acid can act as a buffer. Many aqueous buffers are well known in the art, including phosphate buffers (e.g., $Na_2HPO_4$, $NaH_2PO_4$) citrate buffers (citric acid and sodium citrate, optionally with HCl to further adjust the pH), acetate buffers (acetic acid and sodium acetate), and the like, which can be obtained from commercial suppliers such as Sigma-Aldrich Chemical Co. (St. Louis, Mo.) (see Products for Life Science Research, 2008-2009 Edition, Sigma-Aldrich). Additional buffers that can be used with the amphiphile described herein are shown in the following table.

| Common Name | $pK_a$ at 25° C. | Buffer Range | Specific Compound Name |
|---|---|---|---|
| TAPS | 8.43 | 7.7-9.1 | 3-{[tris(hydroxymethyl)methyl]amino}propanesulfonic acid |
| Bicine | 8.35 | 7.6-9.0 | N,N-bis(2-hydroxyethyl)glycine |
| Tris | 8.06 | 7.5-9.0 | tris(hydroxymethyl)methylamine |
| Tricine | 8.05 | 7.4-8.8 | N-tris(hydroxymethyl)methylglycine |
| HEPES | 7.48 | 6.8-8.2 | 4-2-hydroxyethyl-1-piperazineethanesulfonic acid |
| TES | 7.40 | 6.8-8.2 | 2-{[tris(hydroxymethyl)methyl]amino}ethanesulfonic acid |
| MOPS | 7.20 | 6.5-7.9 | 3-(N-morpholino)propanesulfonic acid |
| PIPES | 6.76 | 6.1-7.5 | piperazine-N,N'-bis(2-ethanesulfonic acid) |
| Cacodylate | 6.27 | 5.0-7.4 | dimethylarsinic acid |
| MES | 6.15 | 5.5-6.7 | 2-(N-morpholino)ethanesulfonic acid |

Buffers or buffer systems used with the amphiphile described herein will generally be employed to maintain a pH near 7 (e.g., about 5 to about 9, about 6 to about 8, or about 6.5 to about 7.5), however higher or lower pH values (e.g., about 3 to about 11) may be used for working with certain types of membrane proteins, such as extremophiles (e.g., halophiles or acidophiles).

The phrase "treating a protein" with a compound, detergent, or surfactant ("agent") refers to contacting the protein with the agent (e.g., an amphiphile as described herein), and/or combining the protein with an effective amount of the agent under conditions that allow the agent to penetrate, integrate and/or disrupt a protein's current environment in order to solubilize, stabilize, isolate, and/or purify the protein. The conditions can be aqueous and additional reagents, such as buffers, salts, and the like, can be added. Thus, a combination of reagents may be employed in the treatment. The protein may be, for example, in a lipid bilayer or substantially isolated in solution.

Specific values listed herein for radicals, substituents, and ranges, are for illustration only; they do not exclude other defined values or other values within defined ranges for radicals and substituents.

Amphiphiles Of The Invention

Certain amphiphiles presented herein feature carbohydrate-derived hydrophilic groups, which may include branch-points in the hydrophilic group and/or the lipophilic group. A tripod series, TPA-1 to TPA-5, illustrated in FIG. 1, each of which contains the lipophilic tripod found in Tripod A, was investigated.

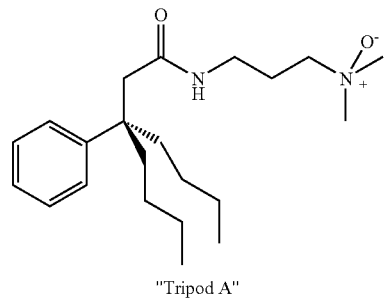

"Tripod A"

Glucoside and maltoside derivatives (TPA-1 and TPA-4, respectively) were prepared and were found to have advantageous solubilization and stabilization properties. In addition, analogues containing branched hydrophilic groups, diglucoside TPA-2, triglucoside TPA-3 and dimaltoside TPA-5, were prepared. These new molecules were evaluated in terms of their ability to solubilize and stabilize membrane protein complexes that comprise the photosynthetic unit in *Rhodobacter* (R.) species of photosynthetic bacteria.

Glycotripod amphiphiles were synthesized by synthetic techniques that readily provided multi-gram quantities. These amphiphiles displayed a considerable range of solubility and aggregation behavior in water. The monoglucoside TPA-1 was not water-soluble without other cosolvents but could be valuable in other systems. The other four glycotripod amphiphiles were highly soluble.

Aqueous solubilization of Orange OT was used to determine critical micelle concentrations (CMC). The values determined for TPA-2 (diglucoside) and TPA-4 (maltoside), 3.6 mM and 4.0 mM, were advantageously comparable to the CMC of A (5.5 mM). Neither TPA-3 nor TPA-5 solubilized Orange OT under the specific conditions employed. Facile self-association of these amphiphiles under these conditions may be hindered by the hydrophilicity and/or steric bulk of the triglucoside and dimaltoside headgroups.

Solubilization Assays

Light harvesting (LH) and reaction center (RC) complexes from photosynthetic bacteria (for example, R. capsulatus) are highly suitable for use in solubilization assays. These complexes, normally embedded in the bacterial membrane, are highly pigmented and several outcomes from an assay are possible, including no degradation, partial degradation or complete degradation upon solubilization, or no solubilization. Thus, graded comparative evaluations could be obtained for a set of candidates such as the amphiphiles described herein.

Figure 2:
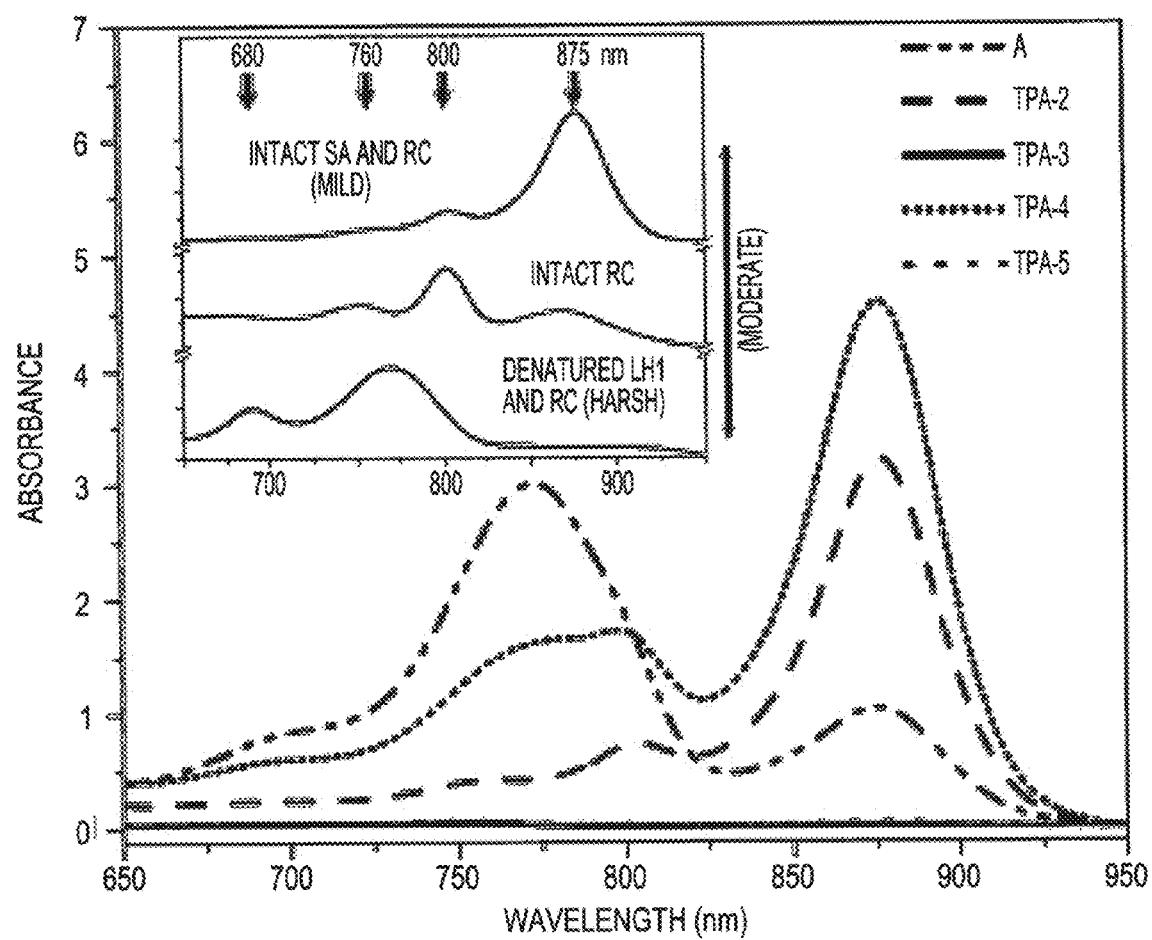
FIG. 2. Spectroscopic comparison of solubilized protein complexes extracted from intracytoplasmic membranes of R. capsulatus using glyco-tripod amphiphiles. In order to remain within the dynamic range of the spectrophotometer (OD<1.5), we used diluted solutions for the more strongly absorbing samples. The absorbance spectra for the original samples, prior to dilution, were then calculated from the observed spectra via multiplication by the appropriate dilution factor. The harshness of the detergent can be judged by the intensity and features in the spectra (representing linear combinations of the spectra of intact SA, intact RC and denatured complexes; inset).

In the engineered strain of R. capsulatus employed, the photosynthetic unit was comprised of a very labile LHI complex and a more resilient RC complex. An ideal amphiphile for this system will extract the intact LHI-RC superassembly from a bacterial membrane preparation and maintain the natural interactions among the components. Amphiphiles with a more disruptive effect will dissociate and denature LHI, leaving only intact RC, and even harsher amphiphiles will cause RC degradation. Each of these various outcomes can be assessed unambiguously via optical spectroscopy (FIG. 2 inset).

Figure 4:
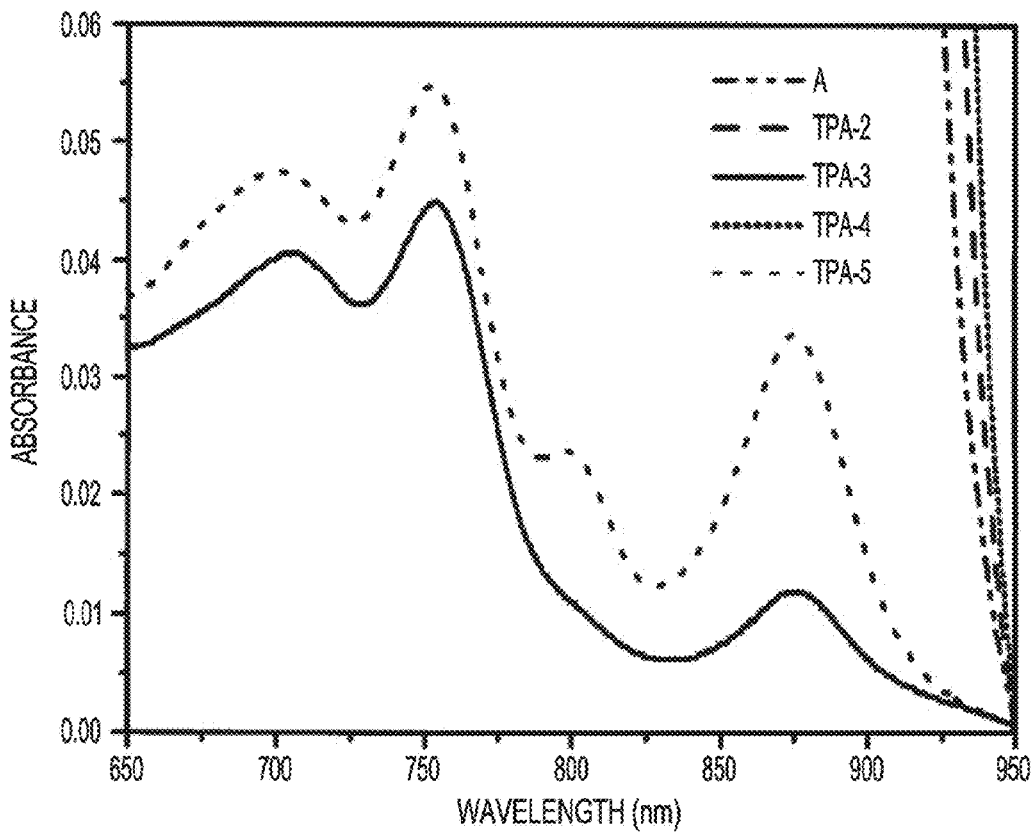
FIG. 4. In support of statements made in the discussion of the efficacy of TPA-3 and TPA-5.

Preliminary studies revealed that A was too harsh to be useful for the preparation of intact superassembly (FIG. 2), because LHI is extensively denatured. The strong absorption near 760 nm after solubilization with Tripod A arises from bacteriopheophytins, i.e., bacteriochlorophyll units that have dissociated from LHI complexes and lost the central Mg ion. TPA-3, on the other hand, was too mild to be useful for this system, as no protein is extracted from the membrane by this amphiphile. TPA-5, too, failed to solubilize Orange OT under the specific conditions employed, but TPA-5 nevertheless solubilized a small proportion of relatively intact LHI-RC superassembly (FIG. 4). TPA-4 extracts a significant proportion of the membrane-embedded protein, but the extracted protein includes a substantial amount of denatured LHI (absorbance in the 750-800 nm region). Thus, TPA-4 is too harsh for this specific system.

Figure 5:
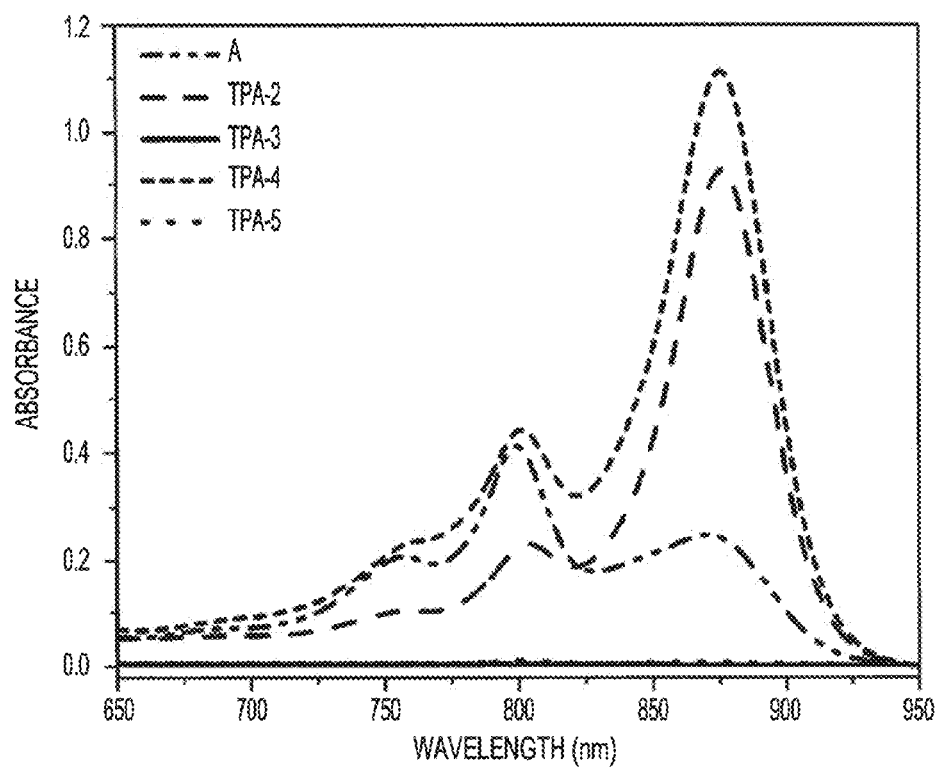
FIG. 5. Spectroscopic comparison of membrane protein complexes purified using affinity chromatography after extraction from intracytoplasmic membranes of R. capsulatus by molecule A and the glycotripod amphiphiles TPA-2, TPA-3, TPA-4, and TPA-5.

TPA-2 displayed excellent properties, in contrast to Tripod A, TPA-3, TPA-4 or TPA-5. Treatment of R. capsulatus membranes with TPA-2 provided intact LHI-RC superassembly in high yield (strong absorption at 875 nm; 875 nm/760 nm absorption ratio ~8; FIG. 2). FIG. 5 illustrates spectroscopic comparison of membrane protein complexes purified using affinity chromatography after extraction from intracytoplasmic membranes of R. capsulatus by Tripod A and the glycotripod amphiphiles TPA-2, TPA-3, TPA-4, and TPA-5. It is noteworthy that TPA-2 and TPA-4 each have two glucose units in the hydrophilic segment and display similar CMC values, but that TPA-2 is clearly superior to TPA-4 with regard to extraction of intact photosynthetic superassembly from the native membrane. This functional difference suggested that incorporation of a branchpoint in the hydrophilic portion leads to significantly improved performance relative to traditional hydrophilic group architectures.

The hydrophilic group branching was then examined in terms of ability to confer distinctive properties in the context of a more conventional lipophilic group. Monopod amphiphiles MPA-1 to MPA-5 (FIG. 1) were prepared, which are analogues of TPA-1 to TPA-5 in which the lipophilic tripod has been replaced by a 12-carbon linear segment. MPA-1 and MPA-4 were not soluble in water without other additives (e.g., cosolvents). CMC values were determined via Orange OT solubilization for MPA-2 (2.4 mM), MPA-3 (4.4 mM) and MPA-5 (1.7 mM). MPA-3 and MPA-5 did not extract any protein from R. capsulatus membranes under the specific conditions employed. MPA-2 extracted a moderate amount of intact LHI-RC superassembly from the native membrane, but MPA-2 is substantially less effective at superassembly solubilization than is TPA-2.

Figure 6:
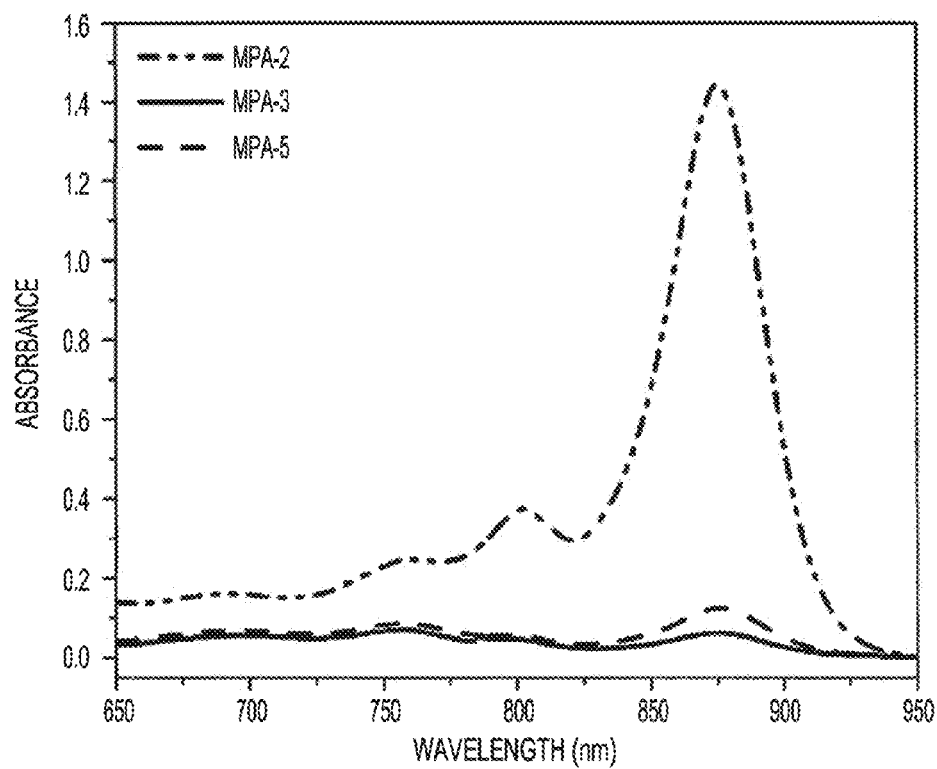
FIG. 6. Spectroscopic comparison of solubilized protein complexes extracted from intracytoplasmic membranes of R. capsulatus by the monopod amphiphiles MPA-2, MPA-3, and MPA-5. Of the hydrophilic variations containing conserved alkyl chains with 12 carbons, the diglucoside (MPA-2) is far superior. MPA-1 and MPA-4 were not screened as they were not soluble in aqueous buffer.

FIG. 6 illustrates spectroscopic comparison of solubilized protein complexes extracted from intracytoplasmic membranes of R. capsulatus by the monopod amphiphiles MPA-2, MPA-3, and MPA-5. Of the hydrophilic variations containing conserved alkyl chains with 12 carbons, the diglucoside (MPA-2) provided excellent properties. MPA-1 and MPA-4 were not screened as they were not soluble in aqueous buffer.

Figure 7:
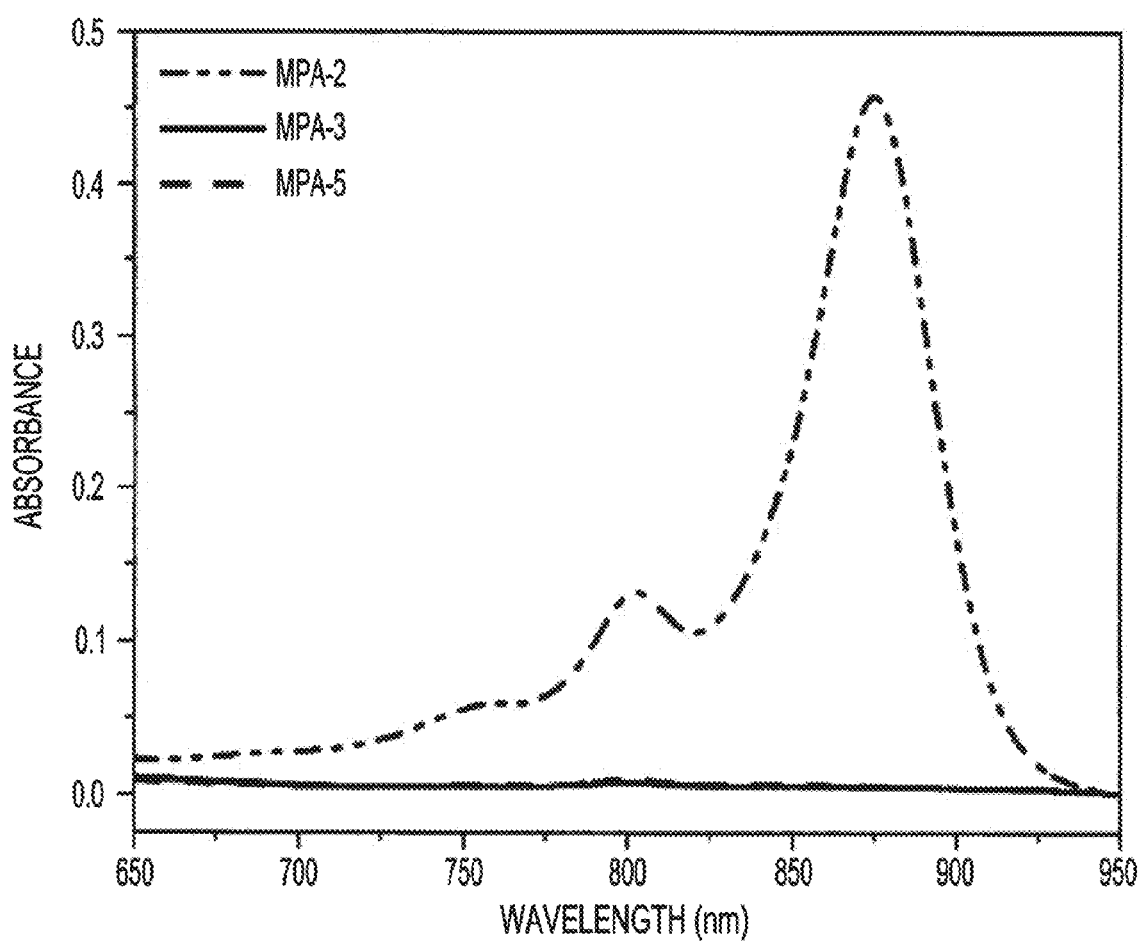
FIG. 7. Spectroscopic comparison of membrane protein complexes purified using affinity chromatography after extraction from intracytoplasmic membranes of R. capsulatus by the monopod amphiphiles MPA-2, MPA-3, and MPA-5.

FIG. 7 illustrates spectroscopic comparison of membrane protein complexes purified using affinity chromatography after extraction from intracytoplasmic membranes of R. capsulatus by the monopod amphiphiles MPA-2, MPA-3, and MPA-5. As seen in FIG. 6, the use of the diglucoside variant (MPA-2) results far greater yield, in comparison to the triglucoside and dimaltoside variants (MPA-3 and MPA-5, respectively).

Variation of alkyl chain length among MPA-2 analogues showed that the 12-carbon length was optimal for this specific system. Analogues containing 8- or 10-carbon segments extracted only lesser amounts of LHI-RC superassembly, while analogues containing 14- or 16-carbon segments extracted no protein under the conditions employed for this system.

Figure 8A:
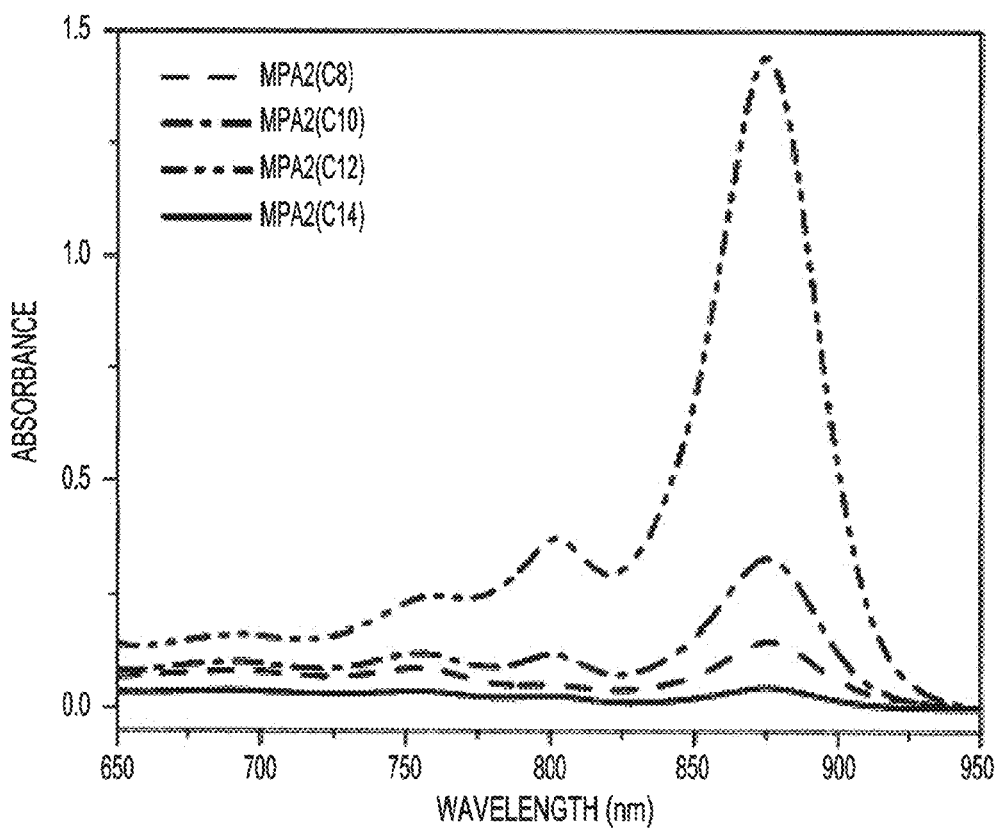
FIG. 8. Spectroscopic comparison (top) of solubilized protein complexes extracted from intracytoplasmic membranes of R. capsulatus by MPA-2 analogues with variations of alkyl chain length. As discussed in the main text, the variant with a 12-carbon chain is most efficient at disrupting the lipid bilayer and solubilizing the LHI-RC supperassembly in functional form. Although MPA-2 extracts nearly 30% of the membrane protein complexes in the sample (bottom), this is only about half as much as is extracted by its tripod analogue, TPA-2 (FIG. 2).
Figure 8B:
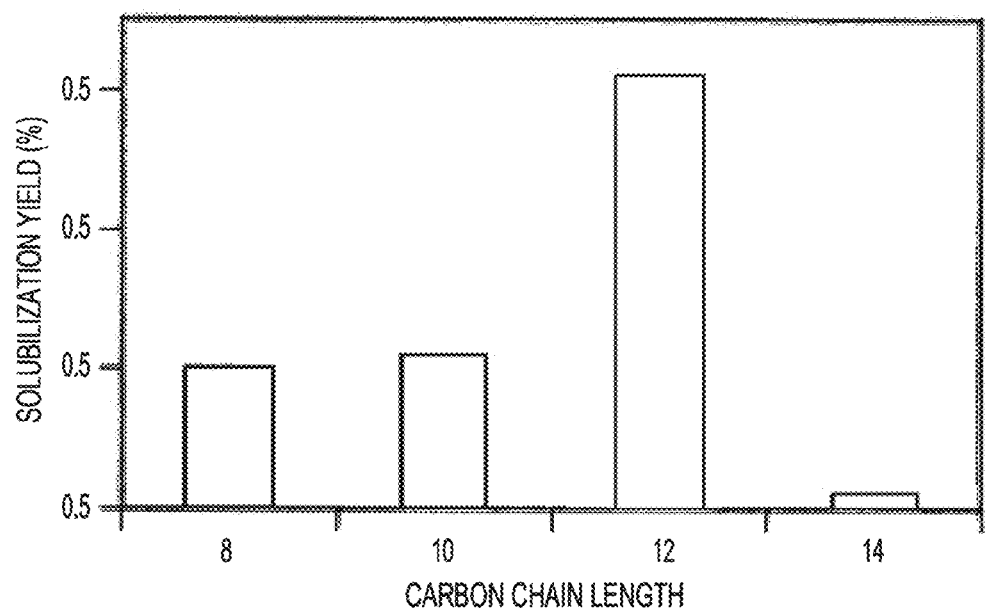
Figure 9:
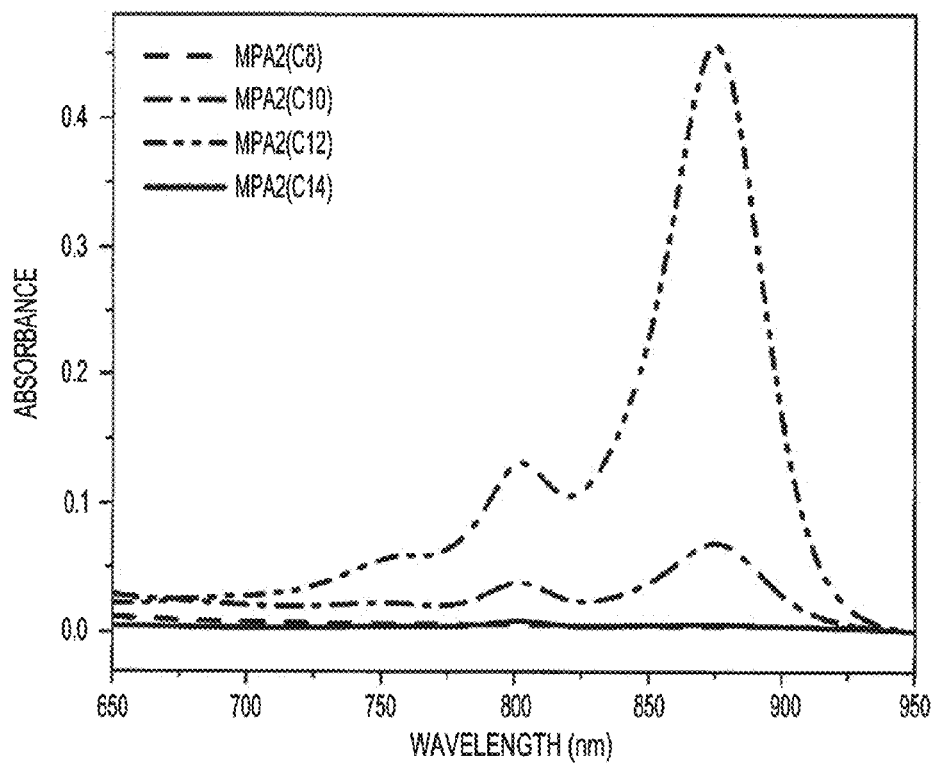
FIG. 9. Spectroscopic comparison of membrane protein complexes purified using affinity chromatography after extraction from intracytoplasmic membranes of R. capsulatus by MPA-2 analogues with variations of alkyl chain length. The superiority of the variant with a 12-carbon chain stems from its high yield of protein extracted from Rhodobacter membranes.

FIG. 8 illustrates spectroscopic comparison (top) of solubilized protein complexes extracted from intracytoplasmic membranes of R. capsulatus by MPA-2 analogues with variations of alkyl chain length. As discussed above, the variant with a 12-carbon chain is most efficient at disrupting the lipid bilayer and solubilizing the LHI-RC supperassembly in functional form in this specific system. MPA-2 extracts nearly 30% of the membrane protein complexes in the sample (bottom), which is, however, less than that extracted by its tripod analogue, TPA-2 (FIG. 2).

Highly effective monopod amphiphile included MPA-2, which features a branched hydrophilic group, indicating that branched hydrophilic groups can have general utility in the development of new detergents. An important aspect of the MPA studies, however, is that highly effective compounds in this series are generally less effective than glycotripod amphiphile, TPA-2, which highlights the effectiveness of branching in both the lipophilic and hydrophilic portions of an amphiphile.

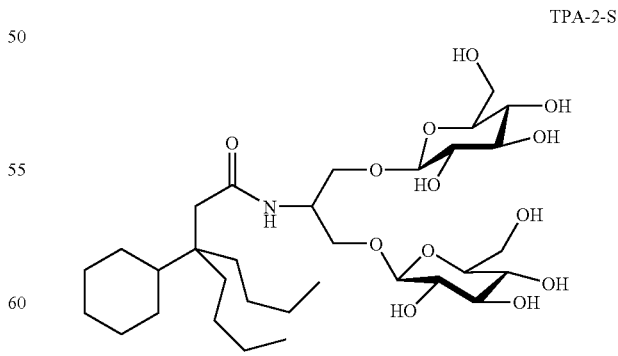

TPA-2-S

The presence of an aromatic ring in TPA-2 may not be appropriate for work with membrane proteins that do not absorb strongly in the visible or near-IR region. Therefore, the saturated analogue TPA-2-S, which lacks a strong UV chromophore, was examined. Orange OT solubilization indicated a CMC of 1.8 mM. TPA-2-S was at least as effective as TPA-2, if not superior, at extracting intact LHI-RC superassembly from R. capsulatus membranes.

Figure 10:
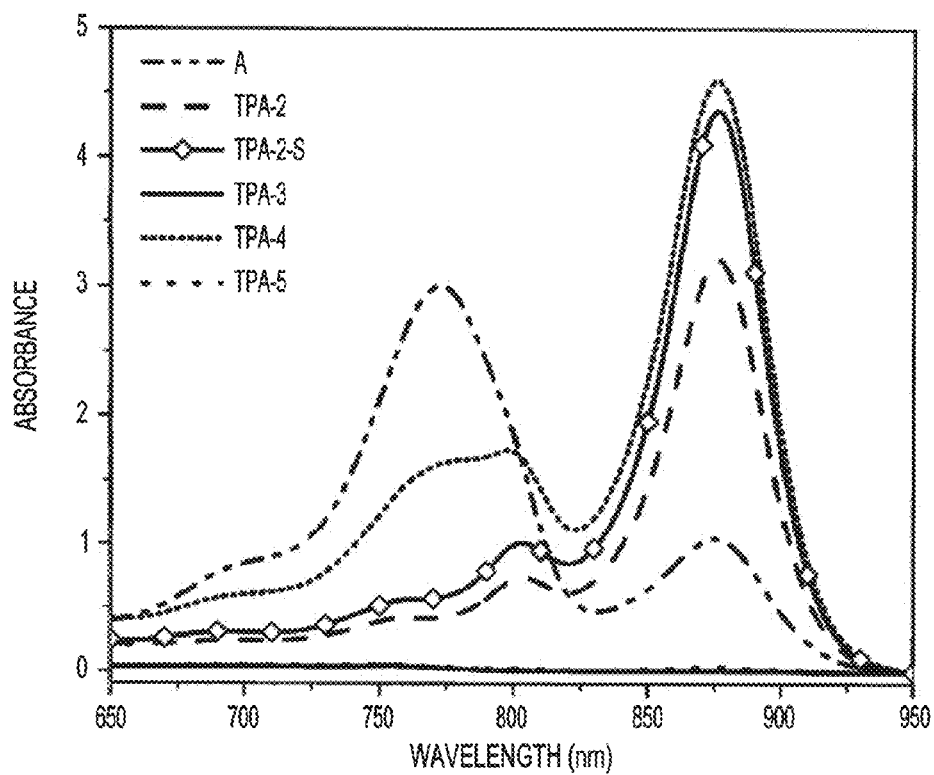
FIG. 10. Spectroscopic comparison of solubilized protein complexes extracted from intracytoplasmic membranes of R. capsulatus by tripod amphiphiles, including the saturated analogue of TPA-2, known as TPA-2-S (also referred to herein as "TPA-21"). TPA-2-S is shown to be as good as or better than TPA-2 at extracting membrane proteins. However, the differences in extraction yield between TPA-2, and TPA-2-S fall within the error of this measurement. In the legend, "A" refers to Tripod A, illustrated above.

FIG. 10 illustrates spectroscopic comparison of solubilized protein complexes extracted from intracytoplasmic membranes of R. capsulatus by tripod amphiphiles, including the saturated analogue of TPA-2, known as TPA-2-S. TPA-2-S was shown to be equal to or superior to TPA-2 at extracting membrane proteins. However, the differences in extraction yield between TPA-2, and TPA-2-S fall within the error of this measurement under the conditions employed.

Figure 11:
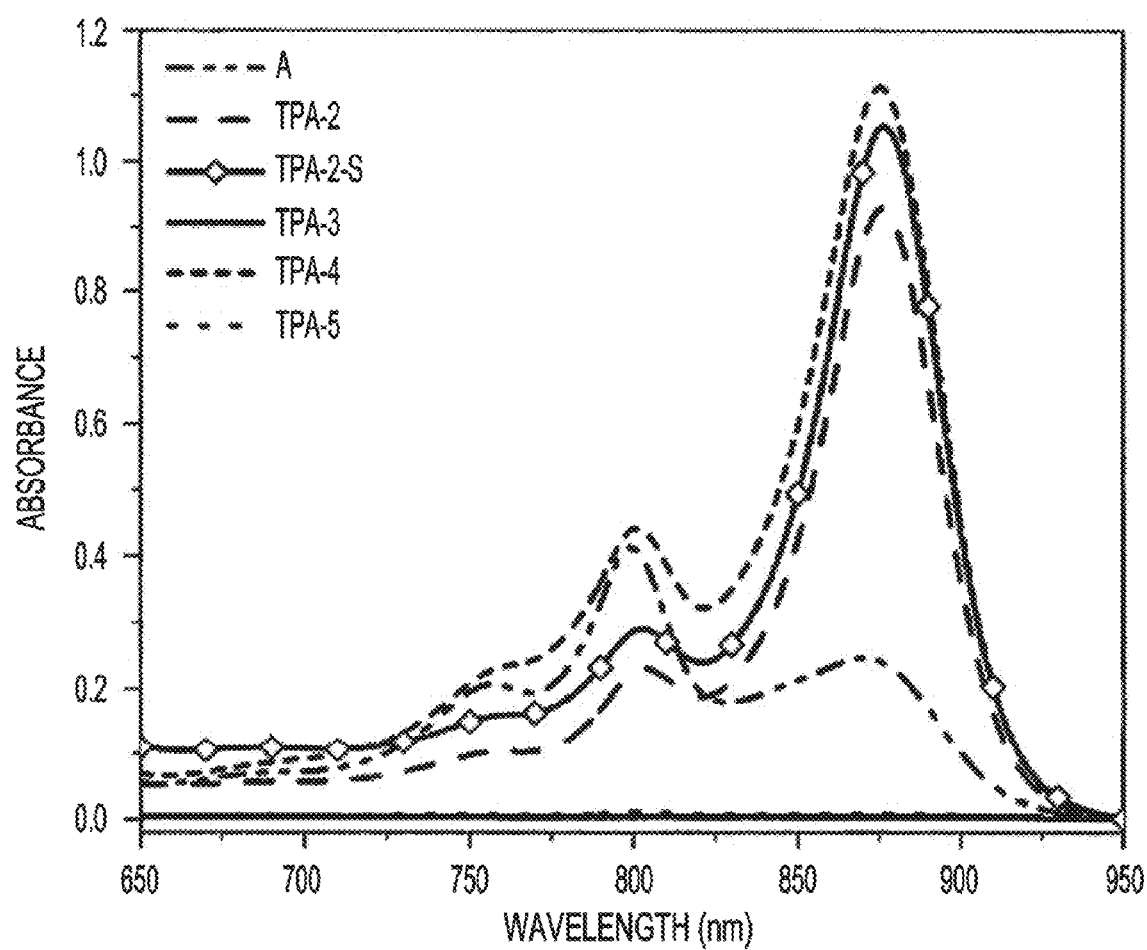
FIG. 11. Spectroscopic comparison of membrane protein complexes purified using affinity chromatography after extraction from intracytoplasmic membranes of R. capsulatus by tripod amphiphiles, including the saturated analogue of TPA-2, known as TPA-2-S. The relative yields of purified protein for the two amphiphiles are similar, as was expected from the yield of solubilized protein observed in FIG. 10. Immediately following purification, micelles of TPA-2-S appear to be at least as stabilizing as those of TPA-2. Upon closer examination, the inventors show from an extensive time course that micelles of the saturated analogue are actually more stabilizing than those of TPA-2 (FIG. 3). In the legend, "A" refers to Tripod A, illustrated above.

FIG. 11 illustrates spectroscopic comparison of membrane protein complexes purified using affinity chromatography after extraction from intracytoplasmic membranes of R. capsulatus by tripod amphiphiles, including the saturated analogue of TPA-2, known as TPA-2-S. The relative yields of purified protein for the two amphiphiles are similar, as was expected from the yield of solubilized protein observed in FIG. 10.

Comparing TPA-2 and TPA-2-S to standard detergents as tools for photosynthetic superassembly solubilization and stabilization revealed clear advantages for the glycotripod amphiphiles. More than 120 conventional detergents were examined with the R. capsulatus system. Dodecylmaltoside (DDM) emerged as one of the most effective detergents, which is consistent with the widespread use of DDM for structural and functional studies of membrane proteins. DDM was comparable to TPA-2 and TPA-2-S in terms of LHI-RC superassembly extraction efficiency. However, a substantial distinction between conventional and glycotripod architectures emerged when the stability of solubilized superassembly was examined.

Figure 3:
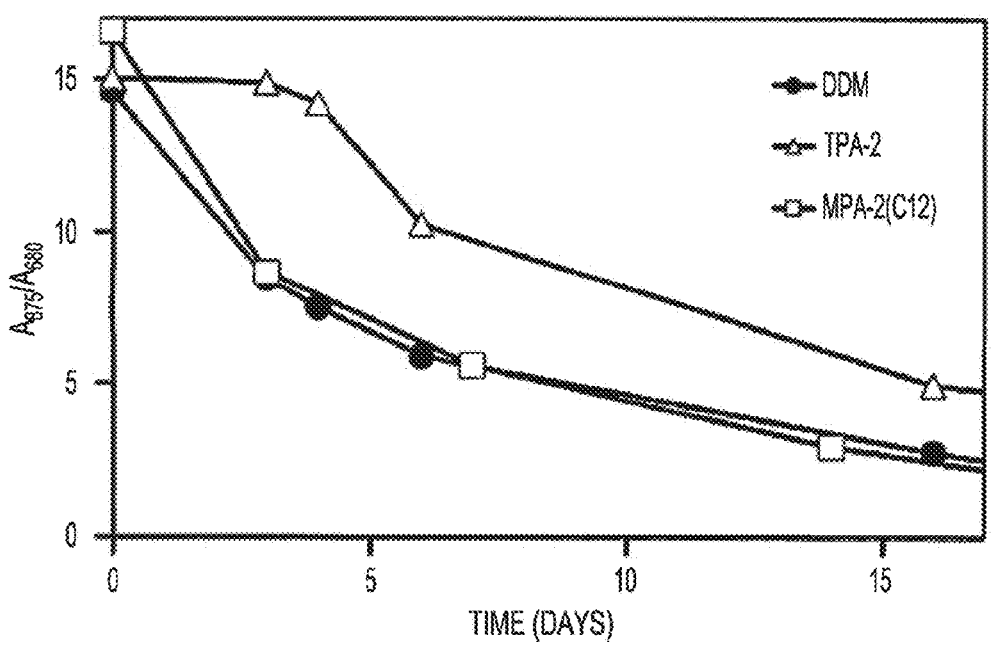
FIG. 3. To monitor the ability of micelles of DDM, TPA-2, and MPA-2(C12) to stabilize membrane protein complexes, spectra of the protein purified by each detergent were recorded as a function of time. The initial spectrum (t=0) was acquired directly after elution of the protein from affinity chromatography. The integrity of the LHI-RC superassembly solubilized by these relatively mild detergents was monitored quantitatively from a scatter-corrected absorbance ratio ($A_{875}/A_{680}$). The ratio of a sample of completely folded and functional supperassembly is >14.5, and this ratio declines dramatically as the multi-subunit complex disassembles and denatures.

Stability was monitored by following the 875 nm/680 nm absorption ratio over a two to three weeks (absorption at 680 nm arises from oxidation of bacteriochlorophyll that has dissociated from LHI protein). As shown in FIG. 3, LHI-RC superassembly solubilized with DDM begins to degrade immediately when incubated at room temperature. In contrast, LHI-RC superassembly solubilized with TPA-2 remains stable for several days, but then later degraded.

These studies demonstrate the importance of branching in the hydrophilic portion of tripod amphiphiles. This new feature complements branching in the lipophilic portion to generate highly effective behavior toward a delicate protein superassembly from R. capsulatus membranes. The new amphiphile, TPA-2, and other amphiphiles described herein, are clearly superior to many conventional biochemical detergents with regard to long-term stability of solubilized LHI-RC superassembly. Accordingly, these amphiphiles, such as the glycotripod amphiphiles, will be a productive source of useful detergents for membrane protein science. The branched carbohydrate units can be generally useful for development of alternative biochemical detergents, because even among the conventional MPA series, effective characteristics were displayed by a branched headgroup (MPA-2). The TPA vs. MPA or DDM comparisons indicate that the new amphiphile design strategies can provide useful alternatives to conventional detergents for membrane protein manipulation.

Compound Characterization and Methods

The Critical Micelle Concentrations (CMCs) of compounds of the invention can be determined by standard techniques known to those of skill in the art. For example, CMCs of the carbohydrate-based amphiphiles described herein can be determined by monitoring uptake of a dye (e.g., Orange OT or 1,6-diphenylhexatriene) with increasing detergent concentration, monitored by UV-visible or fluorescence spectroscopy.

When using the compounds of the invention for solubilization, isolation, purification, stabilization, crystallization, and/or structural determination of membrane proteins, they can be used alone, or in combination with known detergents, such as CHAPS and/or CHAPSO, or other detergents, such as those described in U.S. Pat. No. 6,172,262 (McQuade et al.) and by Hjelmeland in *Methods of Enzymology*, Vol. 124, page 135-164, which are incorporated herein by reference.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

The following examples describe synthesis and characterization of amphiphiles, detergent screening and stabilization measurements.

Example 1

Synthesis and Characterization of Tripod and Monopod Amphiphiles

The preparation of various amphiphiles of the invention is described below. Other amphiphiles can be prepared by varying the techniques and starting materials, as would be readily recognized by one skilled in the art.

Scheme 1. Synthesis of tripod amphiphiles

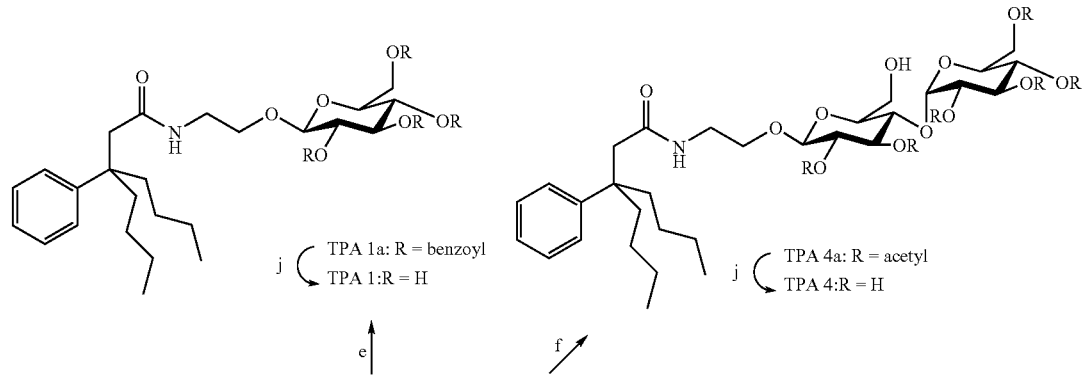

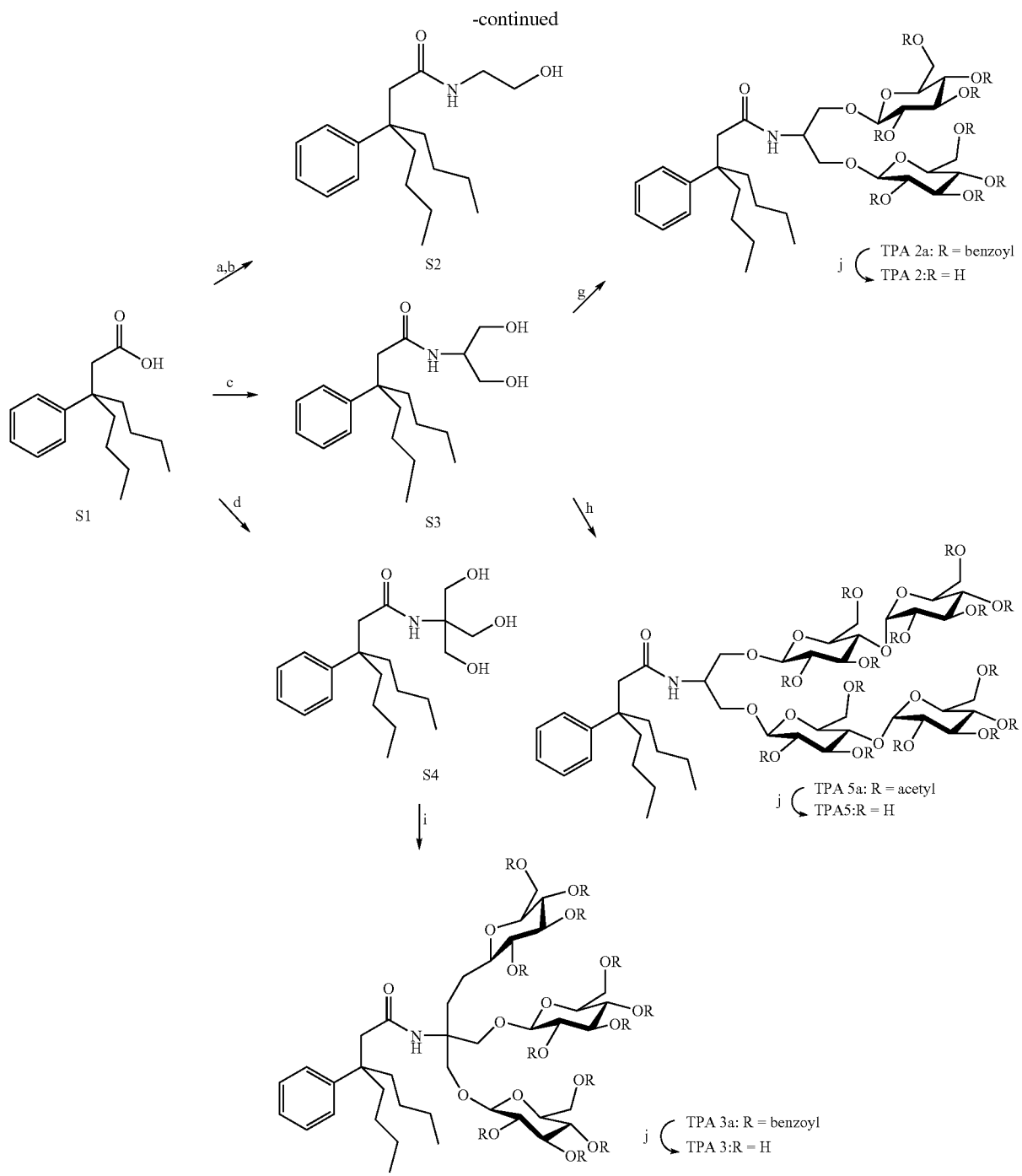

(a) CO₂Cl₂, benzene; (b) catalytic DMF, CH₂Cl₂, room temperature, 85% (two steps); (c) serinol, EEDQ, pyridine, reflux, 78%; (d) TRIS, EEDQ, pyridine, reflux, 80%; (e) 2,3,4,6-tetra-O-benzoyl-α-D-glucopyranosyl bromide (1.2 equiv.), AgOTf, CH₂Cl₂, -35° C. à room temperature, 85%; (f) 1,2-trans-peracetylated maltose (1.2 equiv.), BF3.Et₂O, room temperature, 62%; (g) 2,3,4,6-tetra-O-benzoyl-α-D-glucopyranosyl bromide (2.4 equiv.), AgOTf, CH₂Cl₂, -35° C. à room temperature, 87%; (h) 1,2-trans-peracetylated maltose (2.4 equiv.), BF3.Et₂O, room temperature, 58%; (i) 2,3,4,6-tetra-O-benzoyl-α-D-glucopyranosyl bromide (3.5 equiv.), AgOTf, CH₂Cl₂, -35° C. à room temperature, 90%; (j) NaOMe, MeOH, room temperature, 86% (TPA-1), 89% (TPA-2), 97% (TPA-3), 84% (TPA-4), 95% (TPA-5).

Characterization Data of Various Tripod Amphiphiles.

TPA-1: m.p. 160-162° C.; $^1$H NMR (300 MHz, CDCl₃): δ 7.29-7.25 (m, 4H), 7.16-7.12 (m, 1H), 4.14 (d, J=7.7 Hz, 1H), 3.84 (d, J=11.8 Hz, 1H), 3.72-3.59 (m, 2H), 3.45-3.38 (m, 1H), 3.33-3.10 (m, 6H), 2.54 (s, 2H), 1.84-1.79 (m, 4H), 1.28-1.19 (m, 4H), 1.16-0.98 (m, 4H), 0.87-0.80 (m, 6H); $^{13}$C NMR (75 MHz, CDCl₃): δ 172.5, 146.7, 128.5, 126.7, 126.1, 103.2, 76.6, 76.0, 73.5, 69.7, 68.9, 61.6, 45.8, 43.6, 39.3, 37.3, 37.1, 26.0, 23.5, 14.3; HRMS (ESI): calcd. for $C_{25}H_{41}NO_7Na$ [M+Na]$^+$ 490.2781, found 490.2788.

TPA-2: m.p. (dec.) >204° C.; $^1$H NMR (300 MHz, CD$_3$OD): δ 7.33-7.26 (m, 4H), 7.18-7.12 (m, 1H), 4.19 (t, J=7.5 Hz, 2H), 4.07 (q, J=5.0 Hz, 1H), 3.85 (d, J=12.4 Hz, 2H), 3.75 (dd, J=10.6, 5.0 Hz, 1H), 3.65-3.58 (m, 4H), 3.37-3.23 (m, 11H), 3.17-3.11 (m, 2H), 2.57 (s, 2H), 1.84-1.79 (br t, 4H), 1.29-1.20 (m, 4H), 1.16-1.04 (m, 4H), 0.88-0.82 (m, 6H); $^{13}$C NMR (75 MHz, CD$_3$OD): δ 173.9, 147.9, 129.3, 127.8, 126.9, 105.0, 104.8, 78.1, 75.2, 71.8, 69.6, 62.9, 44.7, 39.1, 38.6, 27.2, 24.5, 14.6; HRMS (ESI): calcd. for C$_{32}$H$_{53}$NO$_{13}$Na [M+Na]$^+$ 682.3415, found 682.3415.

TPA-3: m.p. (dec.) >233° C.; $^1$H NMR (300 MHz, CD$_3$OD): δ 7.32-7.26 (m, 4H), 7.16-7.10 (m, 1H), 4.20 (d, J=7.8 Hz, 3H), 4.11 (d, J=10.1 Hz, 3H), 3.84 (d, J=11.5 Hz, 3H), 3.68-3.60 (m, 6H), 3.35-3.24 (m, 9H), 3.15 (t, J=8.0 Hz, 3H), 2.54 (s, 2H), 1.89-1.72 (m, 4H), 1.30-1.17 (m, 4H), 1.15-0.96 (m, 4H), 0.87-0.79 (m, 6H); $^{13}$C NMR (75 MHz, CD$_3$OD): δ 174.4, 147.8, 129.4, 127.8, 126.9, 104.8, 78.1, 75.2, 71.8, 69.6, 62.9, 60.9, 45.5, 44.7, 39.4, 38.3, 27.1, 24.5, 24.4, 14.6; HRMS (ESI): calcd. for C$_{39}$H$_{65}$NO$_{19}$Na [M+Na]$^+$ 874.4048, found 874.4077.

TPA-4: m.p. 203-205° C.; $^1$H NMR (300 MHz, CD$_3$OD): δ 7.49 (br t, 1H), 7.31-7.24 (m, 4H), 7.16-7.10 (m, 1H), 5.13 (d, J=3.8 Hz, 1H), 4.17 (d, J=7.8 Hz, 1H), 3.89-3.55 (m, 8H), 3.50-3.38 (m, 3H), 3.36-3.07 (m, 5H), 2.54 (s, 2H), 1.81 (t, J=8.0 Hz, 4H), 1.31-1.18 (m, 4H), 1.14-0.98 (m, 4H), 0.83 (td, J=7.4, 2.2 Hz, 6H); $^{13}$C NMR (75 MHz, CD$_3$OD): δ 174.2, 147.9, 129.3, 127.7, 126.8, 104.5, 103.0, 81.4, 77.8, 76.7, 75.2, 74.9, 74.2, 71.6, 69.8, 62.8, 62.3, 44.6, 40.3, 39.1, 38.9, 27.2, 24.5, 14.6; HRMS (ESI): calcd. for C$_{31}$H$_{51}$NO$_{12}$Na [M+Na]$^+$ 652.3309, found 652.3320.

TPA-5: m.p. (dec.) >224° C.; $^1$H NMR (300 MHz, CD$_3$OD): δ 7.32-7.26 (m, 4H), 7.17-7.10 (m, 1H), 5.13 (d, J=3.5 Hz, 2H), 4.17 (d, J=8.5 Hz, 2H), 4.04 (br t, J=5.2 Hz, 1H), 3.89-3.55 (m, 17H), 3.51-3.15 (m, 12H), 3.36-3.07 (m, 3H), 2.56 (s, 2H), 1.83 (br t, J=6.3 Hz, 4H), 1.30-1.18 (m, 4H), 1.14-0.98 (m, 4H), 0.87-0.81 (m, 6H); $^{13}$C NMR (75 MHz, CD$_3$OD): δ 173.9, 147.8, 129.3, 127.8, 126.9, 104.9, 104.6, 103.0, 81.4, 77.8, 76.7, 75.2, 74.9, 74.7, 74.2, 71.6, 69.4, 62.8, 62.4, 44.8, 40.3, 39.1, 38.5, 27.2, 24.5, 14.6; HRMS (ESI): calcd. for C$_{44}$H$_{73}$NO$_{23}$Na [M+Na]$^+$ 1006.4471, found 1006.4501.

Scheme 2. Synthesis of TPA-2-S

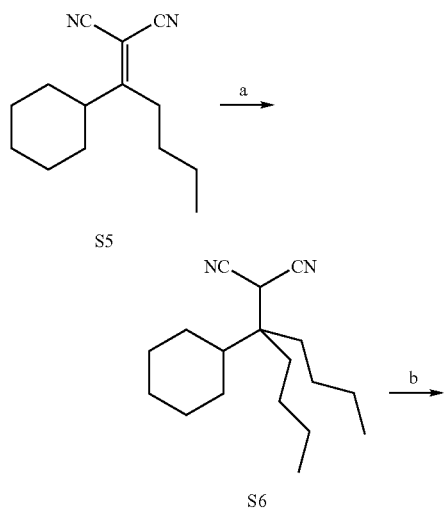

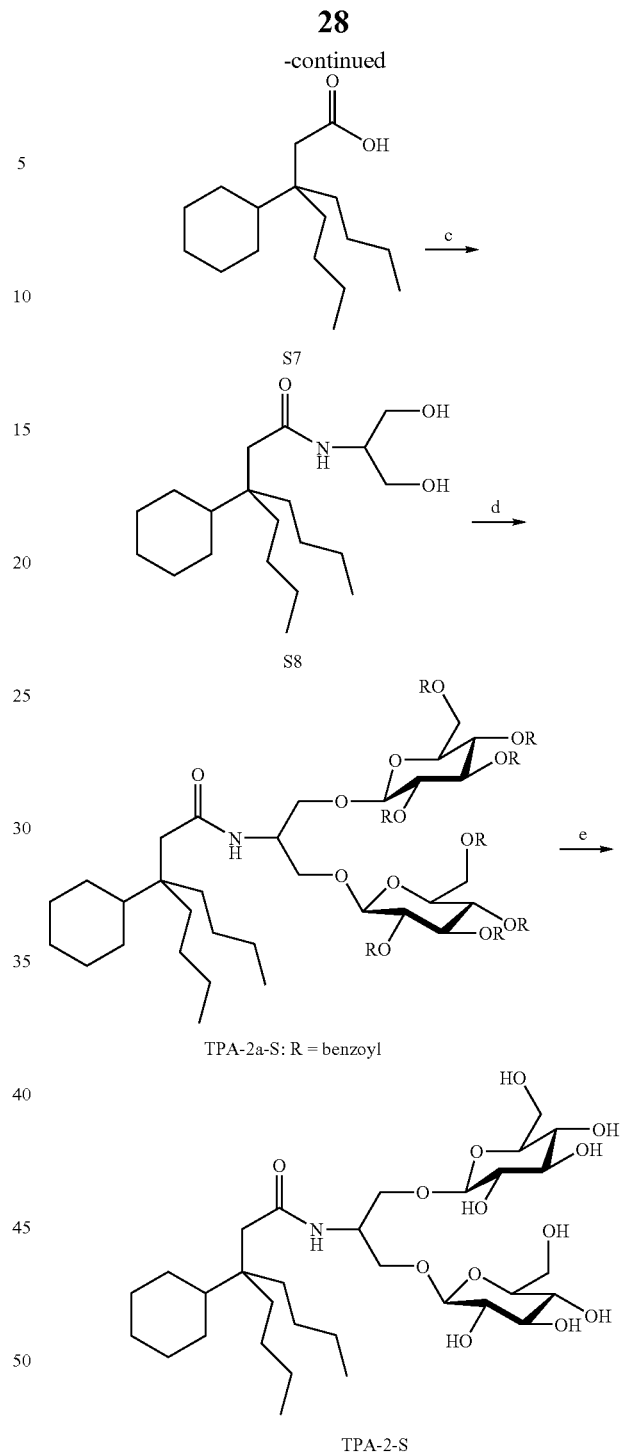

(a) butylMgCl, CuCN, THF, -20° C., 82%; (b) KOH, ethylene glycol, reflux, 92%; (c) serinol, EEDQ, pyridine, reflux, 79%; (d) 2,3,4,6-tetra-O-benzoyl-α-D-glucopyranosyl bromide (2.4 equiv.), AgOTf, CH$_2$Cl$_2$, -35° C.→ room temperature, 85%; (e) NaOMe, MeOH, room temperature, 86%.

Characterization of TPA-2-S.

TPA-2-S: m.p. 193-195° C.; $^1$H NMR (300 MHz, CD$_3$OD): δ 4.26-4.18 (m, 1H), 3.97 (dd, J=9.6, 4.6 Hz, 1H), 3.90-3.86 (m, 4H), 3.70-3.56 (m, 3H), 3.40-3.14 (m, 8H), 2.13 (s, 2H), 1.84-1.60 (m, 5H), 1.54-1.36 (m, 4H), 1.36-1.00 (m, 14H), 0.92 (t, J=7.0 Hz, 6H); $^{13}$C NMR (75 MHz, CD$_3$OD): δ 175.5, 105.1, 104.9, 78.1, 75.2, 71.9, 71.8, 69.8, 69.7, 63.0, 62.9, 50.5, 46.7, 43.1, 42.1, 37.0, 28.9, 28.2, 27.6, 25.0, 14.8; HRMS (ESI): calcd. for C$_{32}$H$_{59}$NO$_{13}$Na [M+Na]$^+$ 688.3884, found 688.3876.

Scheme 3. Synthesis of monopod amphiphiles

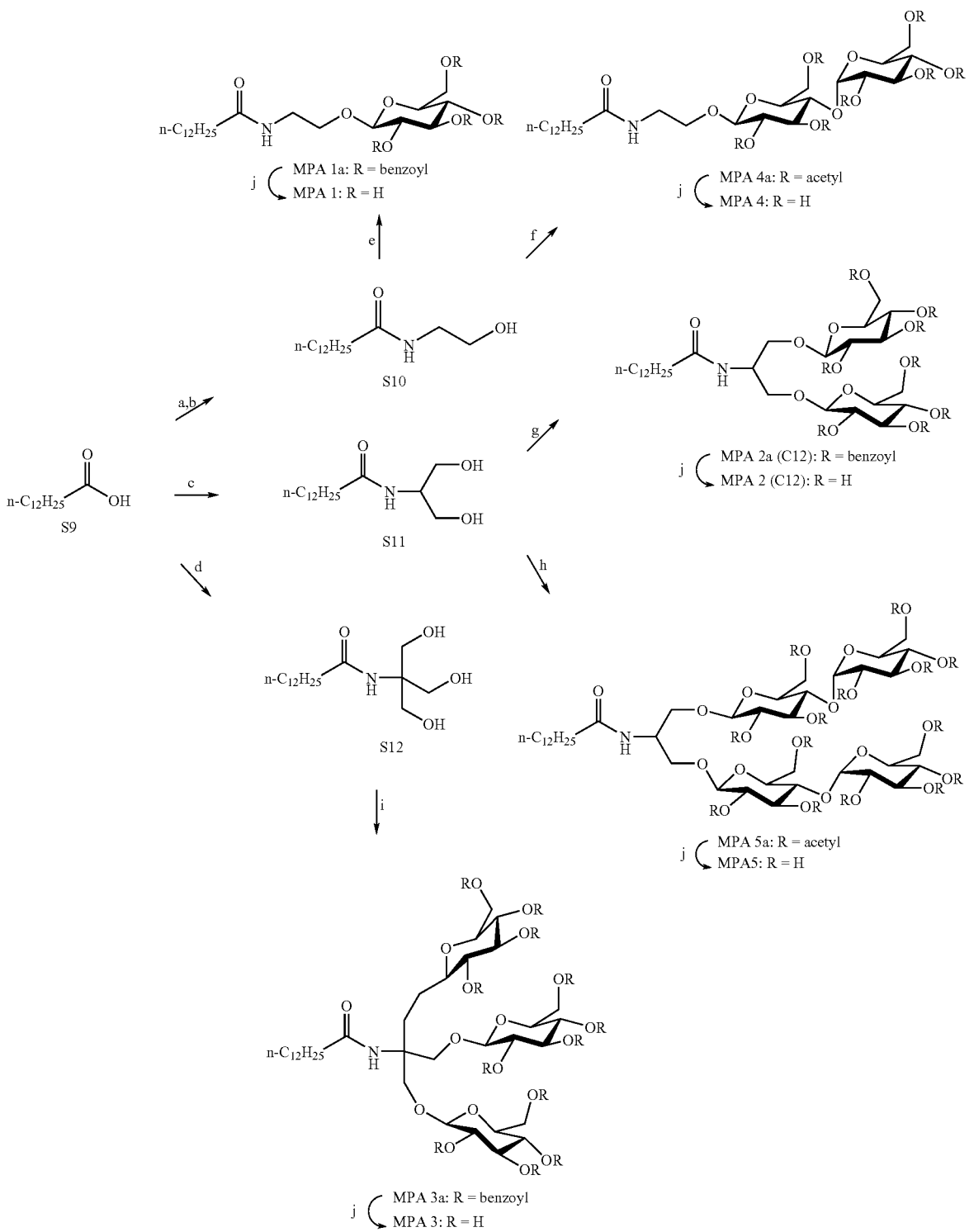

(a) CO₂Cl₂, benzene; (b) catalytic DMF, CH₂Cl₂, room temperature, 86% (two steps); (c) serinol, EEDQ, pyridine, reflux, 78%; (d) TRIS, EEDQ, pyridine, reflux, 82%; (e) 2,3,4,6-tetra-O-benzoyl-α-D-glucopyranosyl bromide (1.2 equiv.), AgOTf, CH₂Cl₂, -35° C. à room temperature, 76%; (f) 1,2-trans-peracetylated maltose (1.2 equiv.), BF₃·Et₂O, room temperature, 59%; (g) 2,3,4,6-tetra-O-benzoyl-α-D-glucopyranosyl bromide (2.4 equiv.), AgOTf, CH₂Cl₂, -35° C. à room temperature, 80%; (h) 1,2-trans-peracetylated maltose (2.4 equiv.), BF₃·Et₂O, room temperature, 55%; (i) 2,3,4,6-tetra-O-benzoyl-α-D-glucopyranosyl bromide (3.5 equiv.), AgOTf, CH₂Cl₂, -35° C. à room temperature, 78%; (j) NaOMe, MeOH, room temperature, 86% (MPA-1), 84% (MPA-2), 89% (MPA-3), 92% (MPA-4), 96% (MPA-5).

Characterization of Monopod Amphiphiles.

MPA-1: m.p. 159-161° C.; $^1$H NMR (300 MHz, CD$_3$OD): δ 4.27 (d, J=7.7 Hz, 1H), 3.94-3.84 (m, 2H), 3.68-3.61 (m, 2H), 3.50-3.42 (m, 1H), 3.38-3.25 (m, 4H), 3.19 (dd, J=9.0, 8.0 Hz, 1H), 2.19 (t, J=7.6 Hz, 2H), 1.64-1.54 (m, 2H), 1.28 (br s, 18H), 0.89 (t, J=7.0 Hz, 3H); $^{13}$C NMR (75 MHz, CD$_3$OD): δ 176.6, 104.7, 78.1, 75.3, 71.8, 69.8, 62.9, 40.7, 37.3, 33.2, 30.9, 30.8, 30.6, 30.5, 27.2, 23.9, 14.6; HRMS (ESI): calcd. for C$_{21}$H$_{41}$NO$_7$Na [M+Na]$^+$ 442.2781, found 442.2776.

MPA-2(C12): m.p. 189-191° C.; $^1$H NMR (300 MHz, CD$_3$OD): δ 4.29 (t, J=7.2 Hz, 2H), 4.25 (m, 1H), 3.97 (dd, J=10.0, 5.2 Hz, 1H), 3.86 (d, J=11.5 Hz, 2H), 3.92-3.77 (m, 2H), 3.65 (dd, J=12.6, 2.7 Hz, 3H), 3.38-3.25 (m, 5H), 3.18 (t, J=8.3 Hz, 2H), 2.21 (t, J=7.7 Hz, 2H), 1.65-1.55 (m, 2H), 1.28 (br s, 18H), 0.89 (t, J=6.9 Hz, 3H); $^{13}$C NMR (75 MHz, CD$_3$OD): δ 176.5, 105.0, 78.1, 75.3, 75.2, 71.8, 69.8, 69.7, 62.9, 50.7, 37.3, 33.2, 30.9, 30.8, 30.7, 30.6, 30.5, 27.2, 23.9, 14.6; HRMS (ESI): calcd. for C$_{28}$H$_{53}$NO$_{13}$Na [M+Na]$^+$ 634.3415, found 634.3428.

MPA-3: m.p. (dec.) >192° C.; $^1$H NMR (300 MHz, CD$_3$OD): δ 4.30 (d, J=7.7 Hz, 3H), 4.29 (d, J=10.5 Hz, 3H), 3.87 (t, J=11.6 Hz, 6H), 3.66-3.61 (m, 3H), 3.36-3.24 (m, 9H), 3.17 (t, J=8.2 Hz, 3H), 2.17 (t, J=7.4 Hz, 2H), 1.61-1.51 (m, 2H), 1.27 (br s, 18H), 0.88 (t, J=7.1 Hz, 3H); $^{13}$C NMR (75 MHz, CD$_3$OD): δ 176.9, 105.0, 78.1, 75.2, 71.8, 69.4, 62.9, 61.3, 38.0, 33.2, 30.9, 30.8, 30.7, 30.6, 30.5, 27.0, 23.9, 14.6; HRMS (ESI): calcd. for C$_{35}$H$_{65}$NO$_{19}$Na [M+Na]$^+$ 826.4048, found 826.4059.

MPA-4: m.p. 187-189° C.; $^1$H NMR (300 MHz, CD$_3$OD): δ 5.14 (d, J=4.0 Hz, 1H), 4.28 (d, J=7.6 Hz, 1H), 3.89-3.79 (m, 4H), 3.67-3.58 (m, 5H), 3.56-3.44 (m, 3H), 3.42-3.33 (m, 2H), 3.27-3.14 (m, 2H), 2.18 (t, J=7.4 Hz, 2H), 1.63-1.53 (m, 2H), 1.27 (br s, 18H), 0.88 (t, J=7.1 Hz, 3H); $^{13}$C NMR (75 MHz, CD$_3$OD): δ 176.6, 104.6, 103.1, 81.5, 77.9, 76.8, 75.2, 75.0, 74.8, 74.3, 71.7, 69.8, 62.9, 62.3, 40.7, 37.3, 33.2, 30.9, 30.8, 30.6, 30.5, 27.2, 23.9, 14.6; HRMS (ESI): calcd. for C$_{27}$H$_{51}$NO$_{12}$Na [M+Na]$^+$ 604.3309, found 604.3314.

MPA-5: m.p. (dec.) >203° C.; $^1$H NMR (300 MHz, CD$_3$OD): δ 5.13 (d, J=3.8 Hz, 2H), 4.30 (d, J=7.8 Hz, 2H), 4.26-4.17 (m, 1H), 3.94 (dd, J=10.0, 5.2 Hz, 1H), 3.90-3.72 (m, 8H), 3.69-3.54 (m, 9H), 3.54-3.32 (m, 6H), 3.30-3.17 (m, 3H), 2.18 (t, J=7.6 Hz, 2H), 1.63-1.51 (m, 2H), 1.26 (br s, 18H), 0.87 (t, J=6.8 Hz, 3H); $^{13}$C NMR (75 MHz, CD$_3$OD): δ 176.5, 104.9, 104.7, 103.0, 81.4, 77.8, 76.8, 76.7, 75.2, 74.9, 74.8, 74.3, 71.6, 69.6, 62.9, 62.3, 50.7, 37.3, 33.2, 30.9, 30.8, 30.6, 30.5, 27.2, 23.9, 14.6; HRMS (ESI): calcd. for C$_{40}$H$_{73}$NO$_{23}$Na [M+Na]$^+$ 958.4471, found 958.4444.

Scheme 4. Synthesis of MPA-2 analogues with variations of alkyl chain length

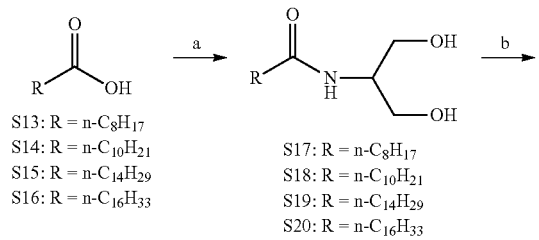

S13: R = n-C$_8$H$_{17}$
S14: R = n-C$_{10}$H$_{21}$
S15: R = n-C$_{14}$H$_{29}$
S16: R = n-C$_{16}$H$_{33}$

S17: R = n-C$_8$H$_{17}$
S18: R = n-C$_{10}$H$_{21}$
S19: R = n-C$_{14}$H$_{29}$
S20: R = n-C$_{16}$H$_{33}$

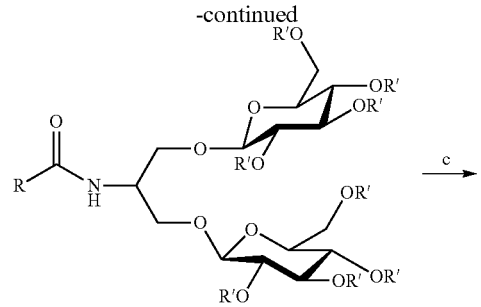

MPA 2a (C8): R = n-C$_8$H$_{17}$
MPA 2a (C10): R = n-C$_{10}$H$_{21}$
MPA 2a (C14): R = n-C$_{14}$H$_{29}$
MPA 2a (C16): R = n-C$_{16}$H$_{33}$

R' = benzoyl

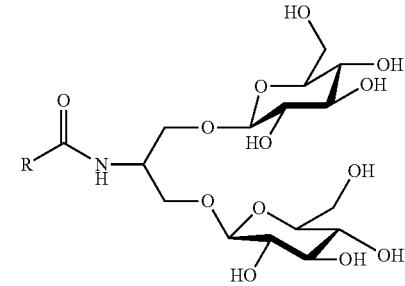

MPA 2 (C8): R = n-C$_8$H$_{17}$
MPA 2 (C10): R = n-C$_{10}$H$_{21}$
MPA 2 (C14): R = n-C$_{14}$H$_{29}$
MPA 2 (C16): R = n-C$_{16}$H$_{33}$ (a) serinol, EEDQ, pyridine, reflux, 80% (S17), 82% (S18), 78% (S19), 75% (S20);
(b) 2,3,4,6-tetra-O-benzoyl-α-D-glucopyranosyl bromide (2.4 equiv.), AgOTf, CH$_2$Cl$_2$, -35° C. → room temperature, 83% (MPA-2a(C8)), 85% (MPA-2a(C10)), 85% (MPA-2a(C14)), 84% (MPA-2a(C16)); (c) NaOMe, MeOH, room temperature, 90% (MPA-2(C8)), 92% (MPA-2(C10)), 89% (MPA-2(C14)), 91% (MPA-2(C16)).

Characterization of MPA-2 Analogues with Variations of Alkyl Chain Length.

MPA-2(C8): m.p. 121-123° C.; $^1$H NMR (300 MHz, CD$_3$OD): δ 4.27 (t, J=7.2 Hz, 2H), 4.22 (m, 1H), 3.96 (dd, J=10.0, 5.1 Hz, 1H), 3.83 (d, J=11.5 Hz, 2H), 3.92-3.77 (m, 2H), 3.62 (dd, J=12.6, 2.7 Hz, 3H), 3.37-3.24 (m, 5H), 3.16 (t, J=8.3 Hz, 2H), 2.18 (t, J=7.7 Hz, 2H), 1.65-1.50 (m, 2H), 1.28 (br s, 10H), 0.87 (t, J=7.0 Hz, 3H); $^{13}$C NMR (75 MHz, CD$_3$OD): δ 176.5, 105.0, 104.9, 78.1, 75.3, 75.2, 71.8, 69.8, 69.7, 62.9, 50.8, 37.3, 33.1, 30.6, 30.5, 27.1, 23.9, 14.6; HRMS (ESI): calcd. for C$_{24}$H$_{45}$NO$_{13}$Na [M+Na]$^+$ 578.2789, found 578.2786.

MPA-2(C10): m.p. 164-166° C.; $^1$H NMR (300 MHz, CD$_3$OD): δ 4.27 (t, J=7.2 Hz, 2H), 4.22 (m, 1H), 3.94 (dd, J=10.0, 5.2 Hz, 1H), 3.83 (d, J=11.5 Hz, 2H), 3.90-3.75 (m, 2H), 3.62 (dd, J=12.6, 2.7 Hz, 3H), 3.36-3.23 (m, 5H), 3.16 (t, J=8.3 Hz, 2H), 2.18 (t, J=7.7 Hz, 2H), 1.63-1.53 (m, 2H), 1.26 (br s, 14H), 0.87 (t, J=6.9 Hz, 3H); $^{13}$C NMR (75 MHz, CD$_3$OD): δ 176.5, 105.0, 104.9, 78.1, 75.3, 75.2, 71.8, 69.8, 69.7, 62.9, 50.7, 37.3, 33.2, 30.8, 30.7, 30.6, 30.5, 27.2, 23.9, 14.6; HRMS (ESI): calcd. for C$_{26}$H$_{49}$NO$_{13}$Na [M+Na]$^+$ 606.3102, found 606.3098.

MPA-2(C14): m.p. (dec.) >198° C.; $^1$H NMR (300 MHz, CD$_3$OD): δ 4.27 (t, J=7.2 Hz, 2H), 4.22 (m, 1H), 3.94 (dd, J=10.0, 5.2 Hz, 1H), 3.83 (d, J=11.5 Hz, 2H), 3.90-3.75 (m, 2H), 3.62 (dd, J=12.6, 2.7 Hz, 3H), 3.36-3.23 (m, 5H), 3.16 (t, J=8.3 Hz, 2H), 2.18 (t, J=7.7 Hz, 2H), 1.63-1.53 (m, 2H), 1.26 (br s, 22H), 0.87 (t, J=6.9 Hz, 3H); $^{13}$C NMR (75 MHz, CD$_3$OD): δ 176.5, 105.0, 104.9, 78.1, 75.2, 71.8, 69.8, 69.7, 62.9, 50.8, 37.3, 33.2, 30.9, 30.8, 30.7, 30.6, 30.5, 27.2, 23.9, 14.6; HRMS (ESI): calcd. for $C_{30}H_{57}NO_{13}Na$ [M+Na]$^+$ 662.3728, found 662.3727.

MPA-2(C16): m.p. (dec.) >202° C.; $^1H$ NMR (300 MHz, $CD_3OD$): δ 4.27 (t, J=7.2 Hz, 2H), 4.22 (m, 1H), 3.94 (dd, J=10.0, 5.2 Hz, 1H), 3.83 (d, J=11.5 Hz, 2H), 3.90-3.75 (m, 2H), 3.62 (dd, J=12.6, 2.7 Hz, 3H), 3.36-3.23 (m, 5H), 3.16 (t, J=8.3 Hz, 2H), 2.18 (t, J=7.7 Hz, 2H), 1.63-1.53 (m, 2H), 1.26 (br s, 26H), 0.87 (t, J=6.9 Hz, 3H); $^{13}C$ NMR (75 MHz, $CD_3OD$): δ 176.5, 105.0, 104.9, 78.1, 75.3, 75.2, 71.8, 69.8, 69.7, 62.9, 50.8, 37.3, 33.2, 30.9, 30.8, 30.7, 30.6, 30.5, 27.2, 23.9, 14.6; HRMS (ESI): calcd. for $C_{32}H_{61}NO_3Na$ [M+Na]$^+$ 690.4041, found 690.4034.

Example 2

Solubilization and Purification of *Rhodobacter capsulatus* Membrane Proteins

A protocol has been developed to enable researchers to evaluate and determine the efficacy of detergents for use in solubilizing membrane proteins. The resulting classification is generally applicable to a wide range of detergents, including the amphiphiles of the invention. Detergents were tested with homogenized *Rhodobacter capsulatus* membranes containing photosynthetic protein superassemblies. The homogenate used (containing *Rhodobacter capsulatus* RC and LHI) is light sensitive therefore work should be carried out under low intensity light. Starting with protein complexes in their native lipid bilayer, two important detergent properties were tracked, allowing for a strength ranking to be assigned to any given detergent. The protocol provides a method for rapid and systematic assessment of the solubilizing efficiency and stabilizing propensity of detergents targeted for use in membrane protein manipulation.

Amphiphile Screening and Stabilization.

Measurements. The starting material for the screening protocols and stability measurements included specialized photosynthetic membranes from an engineered strain of *Rhodobacter* (R.) *capsulatus*, U43[pUHTM86Bgl] (Kirmaier et. al. 2003. *Journal of physical Chemistry B*. 106: 1799-1808), lacking the LHII light-harvesting complex. Membranes from this strain containing large quantities of the LHI-RC superassembly were isolated in advance, according to methods outlined by Laible and coworkers, and were flash frozen (Laible et al. 1998. *Biophysical Journal*. 74: 2623-2637).

To begin the solubilization and purification process, frozen aliquots of *R. capsulatus* membranes were thawed, homogenized, and equilibrated to 32° C. for 30 minutes. Disruption of the lipid bilayer and solubilization of the membrane protein complexes commenced with the addition of the desired amphiphile (compound of the invention) at a concentration of up to 100-fold higher than its CMC to 1 mL aliquots of the membranes. The efficacies of the amphiphiles saturated at relatively low concentrations, thus the quality and quantity of protein extracted did not change significantly at higher concentrations of amphiphile. For subsequent experiments, the amphiphiles were evaluated at 10-fold CMC during the solubilization step. The conventional detergent, DDM, was used at 100-fold CMC, which is the concentration typically used for membrane protein extraction (e.g., Chang et al., 1998 *Science*. 282: 2220-2226).

The membrane samples were allowed to incubate with the amphiphile for 30 minutes at 32° C. The solubilized material was then separated from the membrane debris in an ultracentrifuge at 315,000×g at 4° C. for 30 minutes. The pellet, containing membrane protein complexes not removed from the lipid bilayer, was resuspended and homogenized with 1 mL of 10 mM Tris buffer (pH 7.8) and 100 mM NaCl. After a UV-Vis-nearIR absorption spectrum was recorded, the resuspended pellet was discarded. The supernatant from the spin was pipetted into a new microcentrifuge tube containing Ni-NTA resin (Qiagen, Inc.; Valencia, Calif.; pre-equilibrated and stored in an equal volume of buffer containing 10 mM Tris, pH 7.8 and 100 mM NaCl). The tubes were then incubated and inverted for 1 hour at 4° C. During this period, only the reaction center can be bound to the Ni-NTA resin because of the engineered hepta-histidine tag on the C-terminus of the M subunit (Goldsmith et al. 1996. *Biochimica et Biophysica Acta*. 1276: 171-175; Pokkuluri et al. 2002. *Biochemistry*. 41: 5998-6007; Kirmaier et al., 2003 *Chemical Physics*. 294: 305-318).

Once binding was complete, samples were loaded onto resin-retaining spin columns (e.g., emptied His Spin Trap™ columns; GE Healthcare). The columns were then inserted into a 2 mL microcentrifuge tube to retain the filtered solution during centrifugation. Samples were rinsed twice with 0.5 mL of amphiphile-containing binding 15 buffer (a 7.8 pH Tris solution containing the amphiphile used for solubilization at its CMC). Finally, protein was eluted into a fresh microcentrifuge tube with three 0.2 mL elution buffer aliquots (this buffer was identical to binding buffer with the addition of 1 M imidazole).

The *R. capsulatus* LHI-RC complexes extracted and purified by this procedure contain large numbers of cofactors that have absorptions at distinct wavelengths, and each component of the LHI-RC superassembly has a different inherent stability outside the lipid bilayer. The solubilization protocol outlined above therefore provides a multifaceted assessment of the efficacy of conventional detergents and novel amphiphiles. UV-Vis absorption spectroscopy data obtained at various stages of the protocol allow one to determine which protein components have degraded at these stages. The results reveal the relative potency of amphiphiles in disrupting a lipid bilayer and subsequently stabilizing the photosynthetic superassembly or subunits thereof. The disruption potential was measured as the yield of superassembly extracted during solubilization (or, alternatively and more precisely, as the absence of superassembly in the pellet from the spin following solubilization).

The stabilizing propensity was determined from the spectra of the purified protein. An amphiphile was judged to be mild and stabilizing if it allowed the purification of fully intact LHI-RC superassembly (dominant absorption band at 875 nm). An amphiphile was judged to be strong and destabilizing if it resulted in little or no purified protein with absorption in the near IR, or led to isolation of the intact RC (which is relatively robust) in the absence of LHI. In this latter case, the RC was often damaged, as indicated by a large absorption at 760 nm (released co-factors) or dominant absorption at 800 nm with a shoulder at 850 nm, which indicates that the functional RC remains but it has lost a lipid that is normally bound tightly when the RC resides in its native lipid bilayer (Wang et al., 1994. Photosynthesis Research. 42: 203-215). An amphiphile was judged to be of intermediate strength if it allowed for the purification of fully intact RC with damaged or missing LHI (dominant absorption at 800 nm with a shoulder at 875 nm; damaged LHI still bound to RC absorbs at 760 nm).

Similar criteria and protocols were used to judge the ability of amphiphiles to maintain solubilized and purified superassembly for extended periods. In this case, UV Vis-nearIR spectra were recorded at regular intervals. The degradation of the material could be monitored with the $A_{875}/A_{680}$ absorbance ratio, which decreased with time and sample integrity as the dominant 875 nm absorption of intact LHI disappeared and a 680 nm band appeared, indicating the presence of unbound, oxidized cofactors.

Protein Solubilization and Purification Using Amphiphiles.

Figure 12:
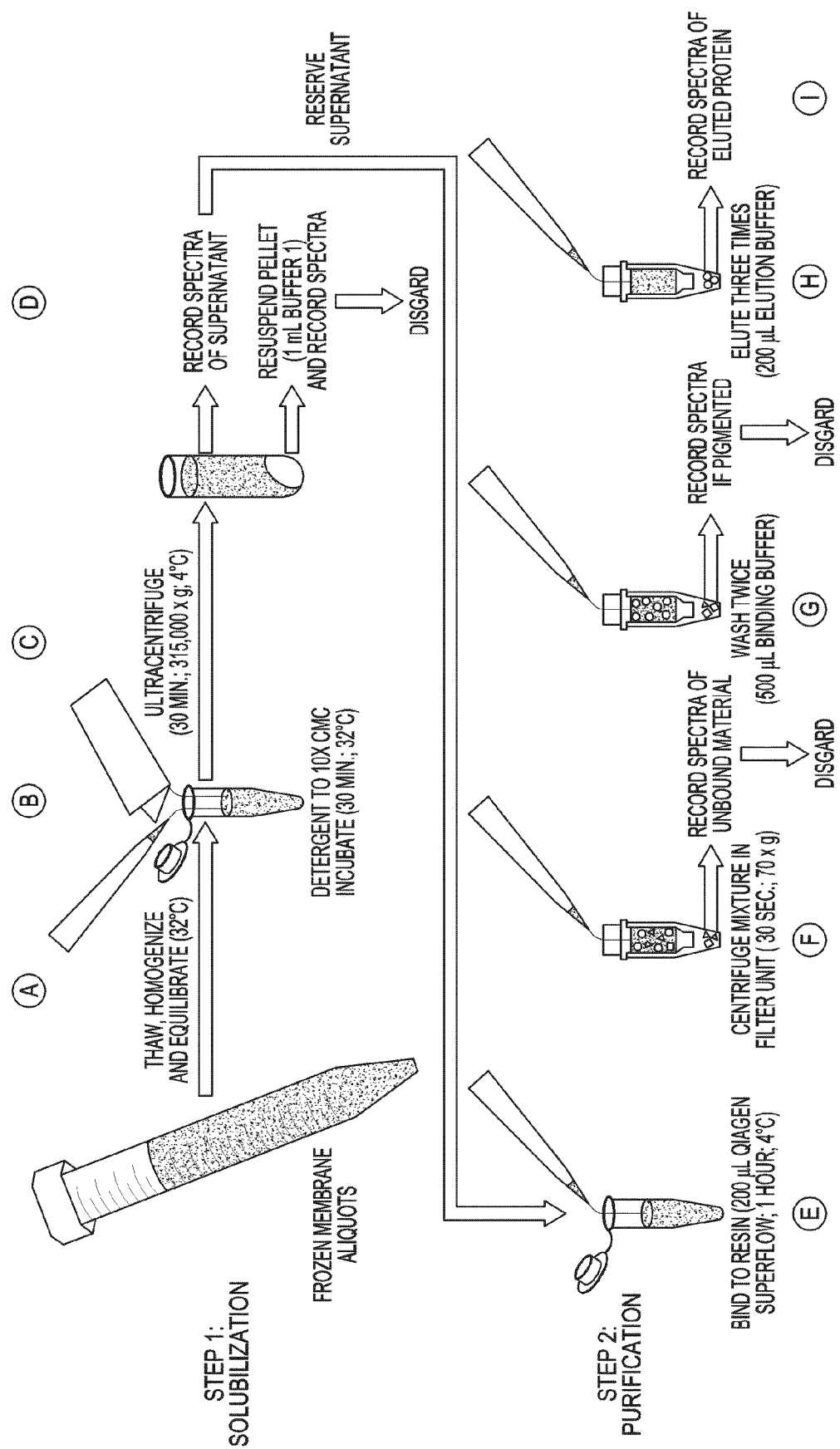
FIG. 12. Illustration of the solubilization and purification steps employed by the inventors in the assay described in Example 2.
Figure 13:
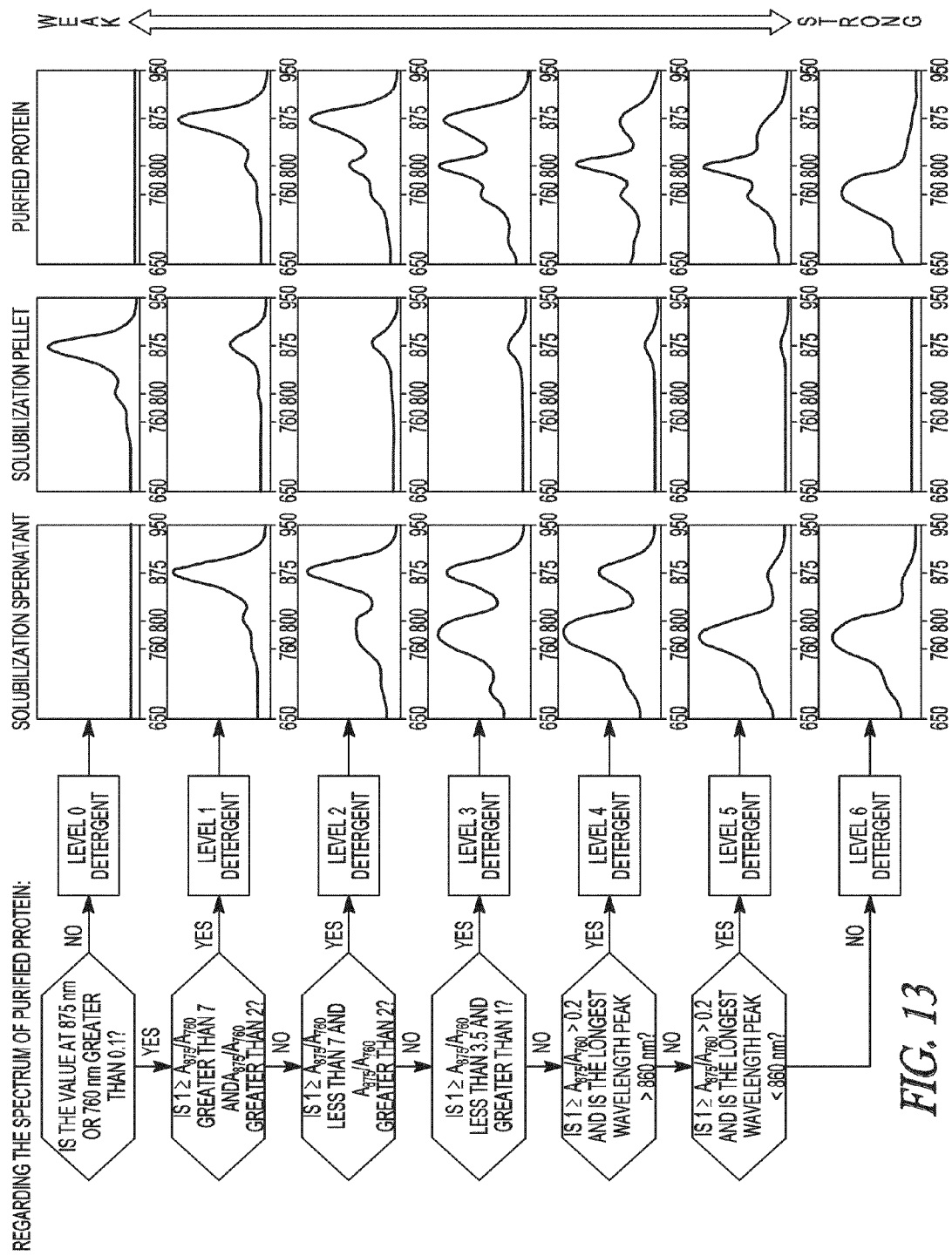
FIG. 13. A flow chart depicting the decision tree utilized by the inventors for classification of amphiphilic compounds in the assay described in Example 2.
Figure 14B:
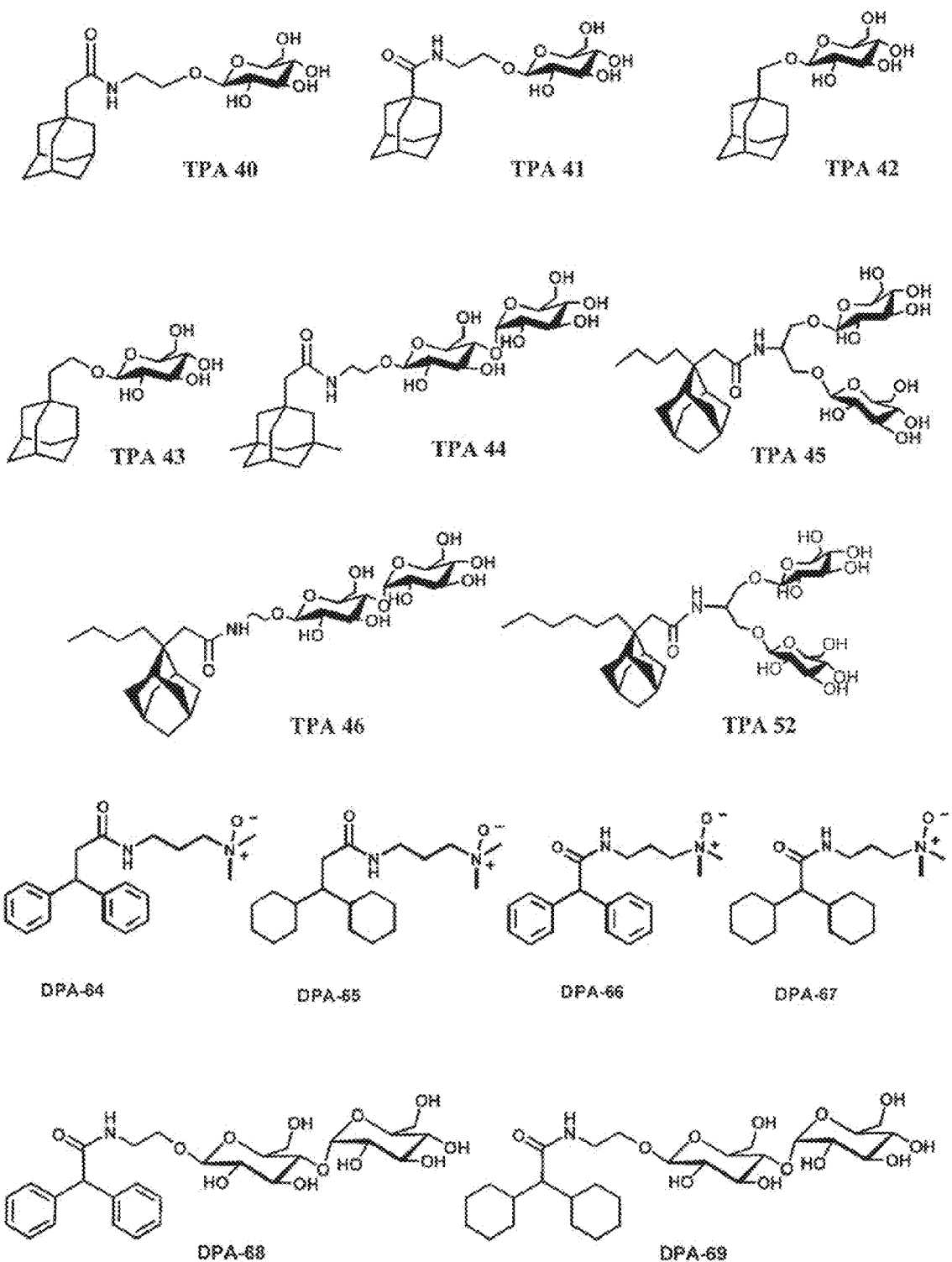

First, solubilization (illustrated in "STEP 1" of FIG. 12) denotes the ability of a surfactant to penetrate, integrate and disrupt a lipid bilayer. This ability is demonstrated by the intensity of the spectral absorption bands of the Solubilization Supernatant (SS) and the Solubilization Pellet (SP). Secondly, the ability of micelles of the test surfactant to stabilize a membrane protein outside of a lipid bilayer can be assayed. For the second type of rating (illustrated in "STEP 2" of FIG. 12), spectra of the Purified Protein (PP) are used. Thus, FIG. 12 provides a graphical depiction of the following detailed steps for protein solubilization and purification, and the procedure for assigning a level to a particular detergent is illustrated in the flowchart of FIG. 13.

Step 1: Solubilization

The following procedure can be used to evaluate solubilization properties of a detergent. The specific amounts of reagents, times, temperatures, and pH can be varied depending on various experimental factors such as the amount of homogenate available, the amount of detergent available, and the like, as would be readily understood by one skilled in the art.

Solubilization Evaluation Procedure:

A) Thaw a 10 mL aliquot of *Rhodobacter capsulatus* RC homogenate ($OD_{875}$ 7.5). Although the membranes may be homogenized once prior to freezing, use a small volume glass tissue homogenizer to uniformly distribute the membrane suspension a second time after it has completely thawed. Equilibrate the homogenate to an appropriate temperature (32° C.) by inverting the entire sample in an Enviro-Genie® refrigerated incubator (or similar machine that allows inversions at a controlled temperature) for at least 30 minutes.

B) Divide the homogenate into 1 mL aliquots (to allow for ten possible screens for one tube of membrane stock) in microcentrifuge tubes. Add the detergent of interest at 10× CMC. Invert in the Enviro-Genie® refrigerated incubator for 30 minutes at 32° C. Use at least two controls (for example, LDAO and n-dodecyl-β-D-maltopyranoside) and one blank (no detergent) to ensure that data can be reliably evaluated.

C) Place the solubilized membrane suspension in a polycarbonate ultracentrifuge tube. Pellet the membrane debris in a tabletop ultracentrifuge at 315,000×g (for example, an Optima™ TLX tabletop ultracentrifuge; TLA 120.2 rotor; 85K rpm) for 30 minutes at 4° C.

D) Record a spectrum (from 650 nm to 950 nm) of the solubilized supernatant (SS), then reserve the supernatant for purification (STEP 2 below). Using a small glass homogenizer, resuspend the remaining pellet with 1 mL of buffer containing 10 mM Tris, pH 7.8 and 100 mM NaCl. Record a spectrum of the resuspended pellet (SP). Dilute to appropriately remain within the dynamic range of the spectrophotometer employed. The resuspended pellet can be disposed of after the spectrum has been recorded.

The 875 nm peak from the spectrum of the Solubilization Pellet of the blank (no detergent) is used to determine the percentage of complexes that were extracted from samples incubated with detergent. If the 875 nm peak of an experimental sample is at or above 50% of the blank peak, the detergent obtains an "S" rank to indicate the majority of the complexes were extracted after solubilization and reside in the Supernatant. Conversely, a detergent obtains the rank of a "P" if peaks are below 50% of the blank peak, indicating the detergent is too weak to effectively penetrate, integrate and disrupt the lipid bilayer, leaving the majority of the complexes within the Pellet.

Step 2: Purification

E) Transfer each SS from step "D" into fresh and separate microfuge tubes. Invert a stock of Ni-NTA resin (Qiagen, Inc.; Valencia, Calif.; prequilibriated and stored in an equal volume of buffer containing 10 mM Tris, pH 7.8 and 100 mM NaCl) until the beads are completely mixed throughout the storage solution. Then add 200 μL of the Ni-NTA resin to each tube containing SS (so that one obtains 100 μL of resin in the tube). Invert the microfuge tubes containing the SS+resin in an Enviro-Genie® refrigerated incubator (or equivalent) for 1 hour at 4° C. to allow ample time for the histidine-tagged complex to bind to the resin.

F) His-Spin Trap™ columns (GE Healthcare) can be used to purify the protein. These columns are pre-packaged with resin in place. Previous experiments indicated that the resin supplied with the His-Spin Trap™ columns does not bind proteins as well as the Ni-NTA Qiagen resin (necessitating the addition of the Qiagen resin in step "E"). These columns are used for the ease of washing and eluting the Ni-NTA resin, however the resin originally received with these columns is not used in this procedure. If a new His-Spin Trap™ column is being used, remove and discard the top cap and break off the bottom closure. Clean and rinse the column using water so that no resin remains.

Place the column in a 2 mL microcentrifuge tube to collect the liquid during centrifugation. Add 500-600 μL (when maximum column volume is 600 μL) of the SS to the column and centrifuge for 30 seconds at 70×g. Remove the flow-through and reserve it in a separate tube. Add any remaining SS and centrifuge again. Two spin cycles are typically required to centrifuge an entire sample. Combine all of unbound material. Although the flow-through from these spins is not used to determine detergent strength, spectra can be recorded to observe elements that did not bind to the column during purification. These spectrum profiles can also help determine if a particular detergent is interfering with affinity chromatography and is not allowing the histidine-tagged reaction center to properly bind to the nickel-charged resin. Once a spectrum of the unbound material has been recorded, it can be discarded.

G) Wash the column resin by adding 500 μL binding buffer (a 7.8 pH, 10 mM Tris solution containing 1×CMC of the detergent used for solubilization) to the column. Centrifuge for 30 seconds at 70×g. Repeat this step to wash the column a second time. If significant pigmentation is noticed in the column washes, record its spectrum. Otherwise, the eluent may be discarded.

H) Use a new 2 mL microcentrifuge tube for this step. Use of new tubes avoids contamination of the purified protein with any residual material that was rinsed off during the column wash. After the column is placed in a new 2 mL microcentrifuge tube, elute the target protein by subjecting the bound protein and resin to three separate aliquots of 200 μL of elution buffer (the binding buffer with the addition of 1 M imidazole). Centrifuge the column for 30 seconds at 70×g between each addition of elution buffer. If a stock Tris solution already at a pH of 7.8 is being used for the buffers, ensure that the pH of this solution is adjusted again to 7.8 after the addition of imidazole.

I) To facilitate spectroscopy, add 400 μL of binding buffer to the purified protein to adjust the volume of 1 mL. Record a spectrum of the purified protein. The reference is a solution containing 10 mM Tris, pH 7.8. From the spectrum of the purified protein, each detergent can be classified into one of six categories (weak to strong detergent) according to the flowchart in FIG. 13.

TABLE 1

CMC values and classification of TPAs, DPAs, MPAs, and other detergents

| Detergent | M.W. | CMC (mM) | CMC (%) | Level |
|---|---|---|---|---|
| TPA0 | 362.55 | 4.4 | 0.16 | S5 |
| TPA1 | 467.6 | — | — | insoluble |
| TPA2 | 659.76 | 3.6 | 0.24 | S1 |
| TPA3 | 851.93 | n.d. | n.d. | P0 |
| TPA4 | 629.74 | 4 | 0.25 | S2 |
| TPA5 | 984.04 | n.d. | n.d. | P0 |
| TPA6 | 376.58 | 2.1 | 0.08 | S5 |
| TPA7 | 376.58 | 1.9 | 0.07 | P6 |
| TPA8 | 418.66 | 0.36 | 0.015 | P0 |
| TPA9 | 423.61 | 0.35 | 0.015 | P0 |
| TPA10 | 390.6 | 0.77 | 0.03 | P5 |
| TPA11 | 368.6 | 2.7 | 0.1 | S2 |
| TPA12 | 439.12 | 6.8 | 0.3 | P0 |
| TPA13 | 928.02 | 3.7 | 0.34 | P0 |
| TPA14 | 908.04 | 3.4 | 0.31 | P0 |
| TPA15 | 1060.14 | 1.7 | 0.18 | P0 |
| TPA16 | 1040.15 | 3.3 | 0.34 | P0 |
| TPA17 | 908.04 | 1.4 | 0.13 | P0 |
| TPA18 | 1040.15 | 0.3 | 0.03 | P1 |
| TPA19 | 342.6 | 1.8 | 0.06 | S4 |
| TPA20 | 441.4 | — | — | insoluble |
| TPA21 | 665.8 | 1.8 | 0.12 | S1 |
| TPA22 | 858 | 3.7 | 0.32 | P0 |
| TPA23 | 635.8 | — | — | insoluble |
| TPA24 | 990.1 | 1.9 | 0.19 | P1 |
| TPA25 | 639.8 | 4.1 | 0.26 | S1 |
| TPA26 | 609.7 | — | — | insoluble |
| MPA1 | 419.55 | — | — | insoluble |
| C8-MPA2 | 555.6 | 77 | 4.3 | P0 |
| C10-MPA 2 | 583.7 | 8.1 | 0.47 | P0 |
| C12-MPA2 | 611.72 | 2.4 | 0.15 | P1 |
| C14-MPA2 | 639.8 | 0.17 | 0.011 | P0 |
| C16-MPA2 | 667.8 | — | — | insoluble |
| MPA3 | 803.89 | 4.4 | 0.35 | P0 |
| MPA4 | 581.69 | — | — | insoluble |
| MPA5 | 936 | 1.7 | 0.16 | P0 |
| CGT1 | 469.6 | — | — | insoluble |
| CGT2 | 661.7 | 2.6 | 0.17 | P1 |
| CGT3 | 631.7 | 1.9 | 0.12 | S1 |
| Triton-N-oxide | 364.5 | 1.1 | 0.04 | P3 |
| TPA 28 | 785.7 | 0.89 | 0.07 | S1 |
| TPA 29 | 611.7 | 12.6 | 0.77 | S1 |
| TPA 30 | 581.7 | 6.9 | 0.4 | S2 |
| TPA 31 | 673.8 | 2.4 | 0.16 | S1 |
| TPA 32 | 701.8 | 1.3 | 0.091 | S1 |
| TPA 33 | 715.9 | 0.42 | 0.03 | S1 |
| TPA 34 | 735.9 | 0.14 | 0.01 | P2 |
| TPA 35 | 687.8 | 1.2 | 0.083 | S1 |
| TPA 36 | 715.9 | 0.56 | 0.04 | S1 |
| TPA 37 | 639.8 | — | — | insoluble |
| TPA 38 | 555.7 | — | — | insoluble |
| TPA 39 | 527.6 | 76.4 | 4.03 | N.Y. |
| TPA 40 | 399.5 | — | — | N.Y. |
| TPA 41 | 385.5 | 180 | 6.9 | N.Y. |
| TPA 42 | 328.4 | — | — | insoluble |
| TPA 43 | 342.4 | — | — | insoluble |
| TPA 44 | 589.7 | 19.1 | 1.1 | S2 |
| TPA 45 | 647.8 | 6.4 | 0.41 | S1 |
| TPA 46 | 617.7 | 2.6 | 0.16 | S2 |
| TPA 47 | 649.8 | 4.7 | 0.3 | S1 |
| TPA 48 | 619.7 | — | — | insoluble |
| TPA 49 | 691.8 | 0.64 | 0.04 | S1 |
| TPA 50 | 621.7 | 19.2 | 1.19 | P1 |
| TPA 51 | 591.7 | 7.7 | 0.46 | S1 |
| TPA 52 | 675.8 | 1.1 | 0.075 | S1 |
| TPA 53 | 635.7 | 13.8 | 0.88 | S1 |
| TPA 54 | 649.8 | 4.5 | 0.29 | S1 |
| TPA 55 | 601.7 | 13.8 | 0.83 | S1 |
| TPA 56 | 573.6 | 63.8 | 3.7 | N.Y. |

TABLE 1-continued

CMC values and classification of TPAs, DPAs, MPAs, and other detergents

| Detergent | M.W. | CMC (mM) | CMC (%) | Level |
|---|---|---|---|---|
| TPA 57 | 651.8 | 2.25 | 0.15 | S1 |
| TPA 58 | 593.7 | 5.5 | 0.32 | S1 |
| TPA 59 | 591.7 | 7.3 | 0.43 | S2 |
| TPA 60* | 340.5 | 4.5 | 0.15 | S3 |
| TPA 61 | 352.6 | — | — | insoluble |
| TPA 62 | 338.5 | 6 | 0.2 | S3 |
| TPA 63 | 324.5 | 12.8 | 0.42 | S4 |
| DPA 64 | 312.4 | 111 | 3.48 | P3 |
| DPA 65 | 324.5 | 24.7 | 0.8 | S2 |
| DPA 66 | 326.4 | 77.5 | 2.53 | P0 |
| DPA 67 | 338.5 | 4.9 | 0.17 | S2 |
| DPA 68 | 579.6 | 85.3 | 4.95 | P0 |
| DPA 69 | 591.7 | 13.9 | 0.82 | S1 |
| TPA 70 | 699.7 | 8.3 | 0.58 | S1 |
| TPA 73 | 705.9 | 0.21 | 0.014 | P0 |

CMCs were determined by DPH (diphenylhexatriene) or were obtained using Orange OT. N.Y. refers to a value Not determined Yet.

Table 1 shows the efficacy and data for several amphiphiles of the invention. In some embodiments, a lower CMC value can indicate that less detergent is required for manipulating membrane proteins. Lower amounts of detergent can simplify characterization and analysis of membrane proteins.

In Table 1, the column labeled Level indicates whether majority of membrane protein was solubilized into the supernatant (S) or remained in the pellet (P) after ultracentrifugation by the specific amphiphile. Detergent strength of each amphiphile was determined as described above, and as illustrated in FIGS. 12 and 13, with level 1 indicating the mildest detergent strength and level 6 indicating the strongest detergents. Generally, maltosides-derived amphiphiles fall into levels 1 or 2, glucoside-derived amphiphiles fall into levels 3 or 4, and N-oxide-derived amphiphiles fall into level 5, such as in the case of many classical detergents.

Membrane proteins have a wide range of stability outside their native environment. Some membrane proteins are considered to be robust, while others are considered fragile. Mild amphiphiles (e.g., those categorized into levels 1 and 2) will be suitable for fragile membrane protein manipulation, while amphiphiles with intermediate strength (e.g., those categorized into levels 3 and 4) will useful for manipulation of more robust membrane proteins. Even strong amphiphiles (e.g., those categorized into levels 5 and 6) will be applicable to extract and stabilize robust membrane proteins because the three dimensional structure of some membrane proteins, such as OmpA and glycoporin A, have been shown to be maintained in harsh detergents.

The following observations have been made. Level 0 amphiphiles were not typically able to extract the R. capsulatus superassembly from its native membrane. However, this does not indicate that these amphiphiles would not be useful with other membrane proteins. Some level 0 amphiphiles can be very mild. Thus, these amphiphiles could be useful for membrane protein stabilization and crystallization after solubilization of a membrane protein with a classical detergent, using detergent exchange to then employ the level 0 amphiphiles.

Level 0 amphiphiles can also be mixed with other classes of amphiphiles. The resulting mixed micelle could be used to, for example, extract membrane proteins. For example, a level 0 amphiphile and a level 3 amphiphiles can be used together for efficient membrane protein extraction.

Level 1 and level 2 amphiphiles are suitable for extracting fragile membrane proteins in intact structure from their native membranes. After initial solubilization, membrane proteins have been well stabilized for extended periods of time using amphiphiles categorized at these levels. These classes of amphiphiles are also well suited for use in structural analysis, such as crystallographic and NMR spectroscopic analysis.

Level 3 and level 4 amphiphiles can be useful for extracting and stabilizing membrane proteins with intermediate stability, such as bacteriorhodopsin (bR). These classes of amphiphiles provide advantageous properties for crystallization of these membrane proteins with intermediate stability.

Level 5 and level 6 amphiphiles can be useful for extracting and stabilizing robust membrane proteins, such as OmpA and glycoporin A. High quality crystals of these robust membrane proteins suitable for X-ray diffraction can be obtained using amphiphiles categorized at these levels.

New amphiphiles with a range of properties are needed to aid membrane protein research. Certain amphiphiles described herein can be highly effective for handling a specific type or class of membrane protein, and others may be highly suitable for other types or classes of membrane proteins. Accordingly, each specific amphiphile may be more suitable than others for certain purposes, such as solubilization, stabilization, isolation, purification, crystallization, and/or structural determination of membrane proteins, depending on the conditions employed and the desired technique to be performed.

Thus, detergent strength, determined according to the procedures outlined above, and illustrated in FIGS. 12 and 13, can therefore be use to aid a determination of which amphiphile to select for manipulating a specific type of protein. While mild detergents are suitable for manipulating certain membrane proteins, stronger detergents may be necessary for others. The invention therefore provides a range of amphiphiles for use with various types of membrane proteins, including integral membrane proteins and extrinsic membrane proteins. The classification system described herein can aid in determining which amphiphile to select for commencing a particular membrane protein analysis.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. An amphiphilic compound of Formula I:

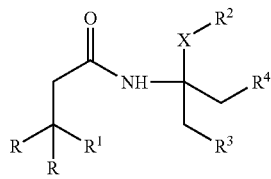

(I)

wherein
each R is independently $C_1$-$C_{16}$ straight or branched alkyl, $C_3$-$C_8$ cycloalkyl, $C_3$-$C_8$ cycloalkenyl, phenyl, biphenyl, or $C_3$-$C_8$ cycloalkyl, $C_3$-$C_8$ cycloalkenyl, phenyl, biphenyl substituted with one, two, or three $C_1$-$C_6$ straight or branched alkyl groups; or the two R groups together with the carbon to which they are attached form a $C_3$-$C_8$ cycloalkyl, a $C_3$-$C_8$ cycloalkenyl, or an adamantyl ring;

$R^1$ is $C_1$-$C_{16}$ straight or branched alkyl, $C_3$-$C_8$ cycloalkyl, $C_3$-$C_8$ cycloalkenyl, phenyl, biphenyl, halophenyl, p-tolyl, adamantyl or $C_3$-$C_8$ cycloalkyl, $C_3$-$C_8$ cycloalkenyl, phenyl, biphenyl, halophenyl, p-tolyl, adamantyl substituted with one, two, or three $C_1$-$C_6$ straight or branched alkyl groups; or R, R, and $R^1$ together with the carbon to which they are attached form an adamantyl ring, optionally substituted with one, two, or three $C_1$-$C_6$ straight or branched alkyl groups;

X is $CH_2$ or a direct bond;

$R^2$ is H, an O-linked $C_6$ glycosyl residue, or an O-linked oligosaccharide comprising two or more glycosyl residues;

$R^3$ is an O-linked $C_6$ glycosyl residue, or an O-linked oligosaccharide comprising two or more glycosyl residues, or a $C_1$-$C_4$ alkyl-(N,N-dimethyl)N-oxide; and $R^4$ is an O-linked $C_6$ glycosyl residue, an O-linked oligosaccharide comprising two or more glycosyl residues, or a $C_1$-$C_4$ alkyl-(N,N-dimethyl)N-oxide.

2. The amphiphilic compound of claim 1 wherein each R is independently ethyl, n-propyl, n-butyl, n-pentyl, n-hexyl, n-heptyl, adamantyl, cyclopentyl, cyclohexyl, cycloheptyl, or cyclooctyl; and $R^1$ is $C_1$-$C_{16}$ n-alkyl, isobutyl, cyclopentyl, cyclohexyl, cycloheptyl, cyclooctyl, phenyl, halophenyl, p-tolyl, p-isopropyl phenyl, p-t-butylphenyl, or p-biphenyl.

3. The amphiphilic compound of claim 2 wherein each R is n-butyl and $R^1$ is phenyl; each R is n-butyl and $R^1$ is cyclohexyl; each R is n-butyl and $R^1$ is isobutyl; each R is n-butyl and $R^1$ is p-iodophenyl; each R is ethyl and $R^1$ is isobutyl; each R is n-butyl and $R^1$ is p-tolyl; each R is n-butyl and $R^1$ is p-isopropyl phenyl; each R is n-butyl and $R^1$ is p-t-butyl phenyl; each R is n-pentyl and $R^1$ is phenyl; or each R is n-hexyl and $R^1$ is phenyl.

4. The amphiphilic compound of claim 1 wherein the compound of Formula I is a compound of Formula II:

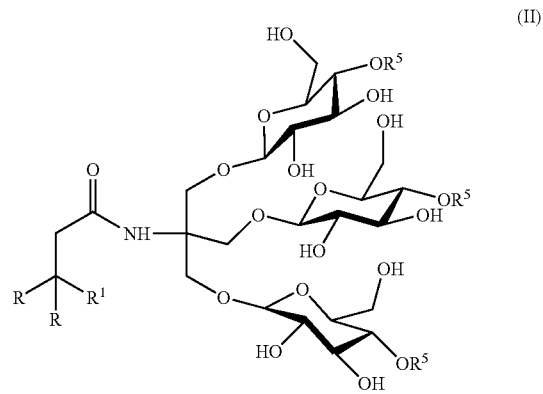

(II)

wherein $R^5$ is H or a $C_6$ glycosyl residue.

5. The amphiphilic compound of claim 1 wherein X is a direct bond and $R^2$ is H.

6. The amphiphilic compound of claim 5 wherein the compound of Formula I is a compound of Formula III:

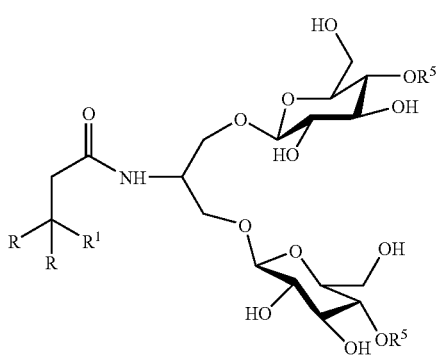

wherein R⁵ is H or a $C_6$ glycosyl residue.

7. The amphiphilic compound of claim 1 wherein one or both of $R^3$ and $R^4$ are O-linked glucose, mannose, galactose, maltose, or sucrose residues.

8. An amphiphilic compound of Formula IV:

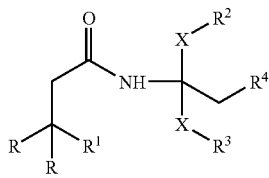

wherein
- one R is H and the other R is $C_1$-$C_{16}$ straight or branched alkyl, $C_3$-$C_8$ cycloalkyl, $C_3$-$C_8$ cycloalkenyl, phenyl, biphenyl, or $C_3$-$C_8$ cycloalkyl, $C_3$-$C_8$ cycloalkenyl, phenyl, biphenyl substituted with one, two, or three $C_1$-$C_6$ straight or branched alkyl groups; or
- the two R groups together with the carbon to which they are attached form an adamantyl ring;
- $R^1$ is $C_1$-$C_{16}$ straight or branched alkyl, $C_3$-$C_8$ cycloalkyl, $C_3$-$C_8$ cycloalkenyl, phenyl, biphenyl, halophenyl, p-tolyl, adamantyl or $C_3$-$C_8$ cycloalkyl, $C_3$-$C_8$ cycloalkenyl, phenyl, biphenyl, halophenyl, p-tolyl, adamantyl substituted with one, two, or three $C_1$-$C_6$ straight or branched alkyl groups; or
- R, R, and $R^1$ together with the carbon to which they are attached form an adamantyl ring, optionally substituted with one, two, or three $C_1$-$C_6$ straight or branched alkyl groups;
- each X is independently $CH_2$ or a direct bond;
- $R^2$ is H, an O-linked $C_6$ glycosyl residue, or an O-linked oligosaccharide comprising two glycosyl residues;
- $R^3$ is H, an O-linked $C_6$ glycosyl residue, or an O-linked oligosaccharide comprising two glycosyl residues; and
- $R^4$ is an O-linked $C_6$ glycosyl residue, or an O-linked oligosaccharide comprising two glycosyl residues.

9. The amphiphilic compound of claim 8 wherein each R is independently ethyl, n-propyl, n-butyl, n-pentyl, n-hexyl, n-heptyl, adamantyl, cyclopentyl, cyclohexyl, cycloheptyl, or cyclooctyl; and
$R^1$ is $C_1$-$C_{16}$ n-alkyl, isobutyl, cyclopentyl, cyclohexyl, cycloheptyl, cyclooctyl, phenyl, halophenyl, p-tolyl, p-isopropyl phenyl, p-t-butylphenyl, or p-biphenyl.

10. An amphiphilic compound wherein the compound is:

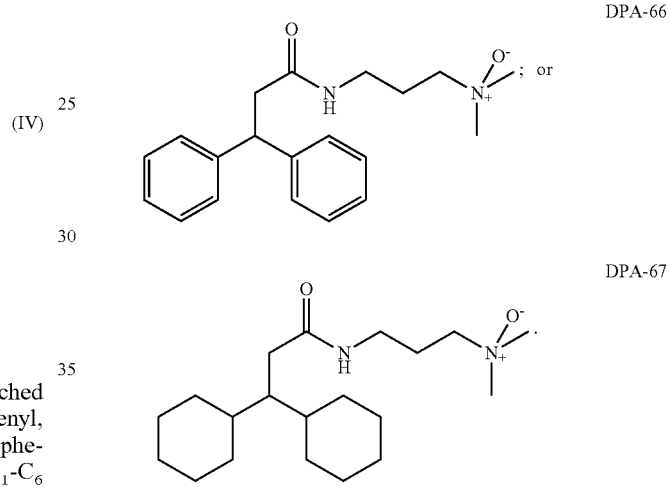

11. The amphiphilic compound of claim 8 wherein the two R groups together with the carbon to which they are attached form an adamantyl ring; $R^1$ is a $C_1$-$C_{16}$ straight or branched alkyl; —X—$R^2$ is direct bond-H; —X—$R^3$ is direct bond-H or —$CH_2$—O-linked $C_6$ glycosyl residue or O-linked oligosaccharide comprising two glycosyl residues.

12. The amphiphilic compound of claim 11 wherein the compound is:

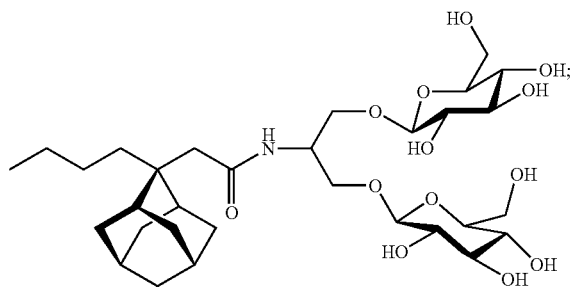

TPA 45

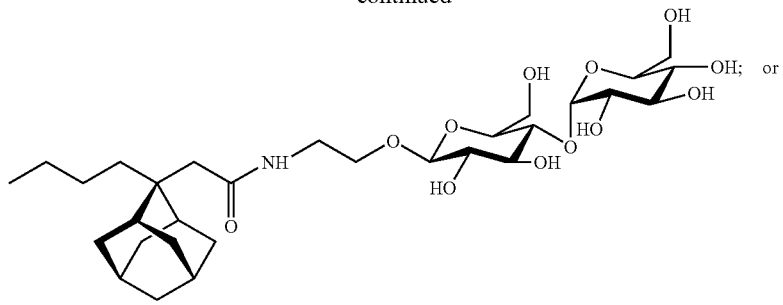

TPA 46

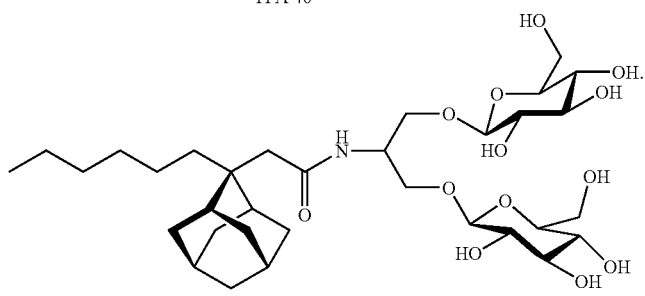

TPA 52

13. The amphiphilic compound of claim 8 wherein the compound of Formula IV is a compound of Formula V:

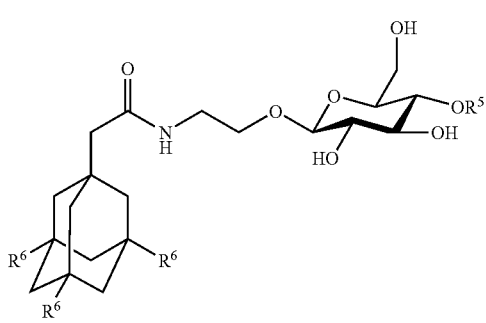

(V)

wherein $R^5$ is H or a $C_6$ glycosyl residue; and
each $R^6$ is independently H or $C_1$-$C_6$ alkyl.

14. The amphiphilic compound of claim 13 wherein the compound is:

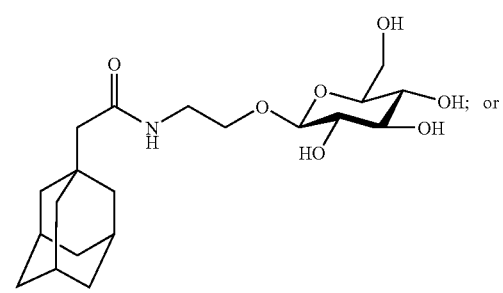

TPA40

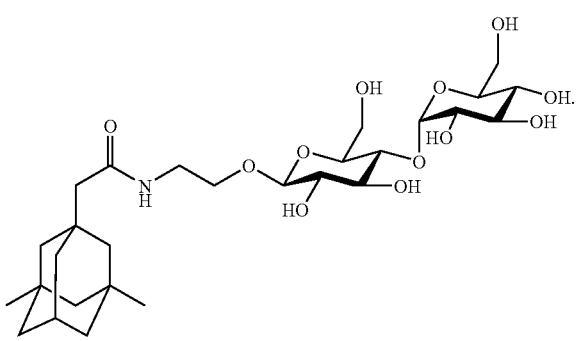

TPA44

15. An amphiphilic compound of Formula VI:

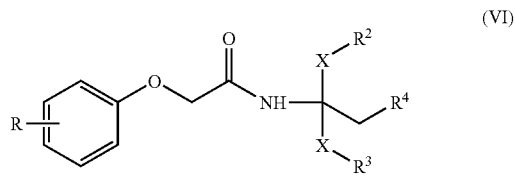

(VI)

wherein R is H, $C_1$-$C_{16}$ straight or branched alkyl, $C_3$-$C_8$ cycloalkyl, $C_3$-$C_8$ cycloalkenyl, phenyl, biphenyl, or $C_3$-$C_8$ cycloalkyl, $C_3$-$C_8$ cycloalkenyl, phenyl, biphenyl substituted with one, two, or three $C_1$-$C_6$ straight or branched alkyl groups;

each X is independently $CH_2$ or a direct bond;

$R^2$ is H, an O-linked $C_6$ glycosyl residue, or an O-linked oligosaccharide comprising two or more glycosyl residues;

$R^3$ is H, an O-linked $C_6$ glycosyl residue, or an O-linked oligosaccharide comprising two or more glycosyl residues, or a $C_1$-$C_4$ alkyl-(N,N-dimethyl)N-oxide; and R[4] is an O-linked $C_6$ glycosyl residue, an O-linked oligosaccharide comprising two or more glycosyl residues, or a $C_1$-$C_4$ alkyl-(N,N-dimethyl)N-oxide.

16. The amphiphilic compound of claim 15 wherein R is a $C_3$-$C_{10}$ branched alkyl.

17. The amphiphilic compound of claim 16 wherein —X—R[2] is direct bond-H; —X—R[3] is direct bond-H or —$CH_2$—O-linked $C_6$ glycosyl residue or O-linked oligosaccharide comprising two or more glycosyl residues; and R[4] is O-linked $C_6$ glycosyl residue or O-linked oligosaccharide comprising two or more glycosyl residues, or a $C_1$-$C_4$ alkyl-(N,N-dimethyl)N-oxide.

18. The amphiphilic compound of claim 17 wherein the compound is:

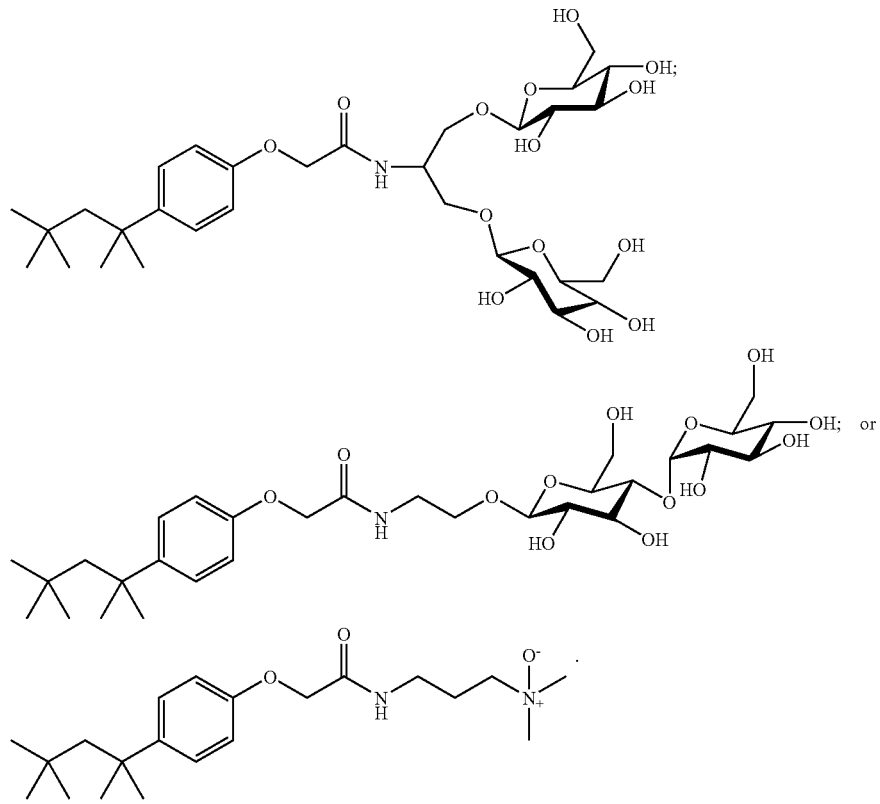

19. A method for solubilizing or stabilizing a membrane protein comprising contacting a protein in an aqueous environment with an effective amount of a compound of claim 1, and
   optionally heating the protein and the compound, to provide the solubilized protein encapsulated in micelles of the compound.

20. A method for solubilizing or stabilizing a membrane protein comprising contacting a protein in an aqueous environment with an effective amount of a compound of claim 8, and
   optionally heating the protein and the compound, to provide the solubilized protein encapsulated in micelles of the compound.

21. A method for solubilizing or stabilizing a membrane protein comprising contacting a protein in an aqueous environment with an effective amount of a compound of claim 15, and
   optionally heating the protein and the compound, to provide the solubilized protein encapsulated in micelles of the compound.

22. The amphiphilic compound of claim 1 wherein the compound is:

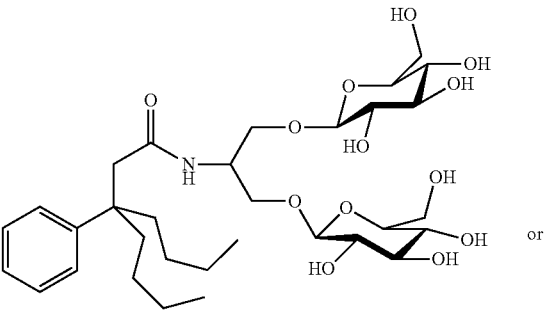

TPA-2

-continued

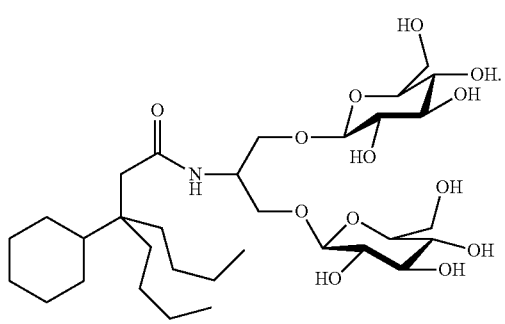

TPA-2-S

* * * * *